(12) United States Patent
Maheshwari et al.

(10) Patent No.: US 11,154,647 B2
(45) Date of Patent: Oct. 26, 2021

(54) TECHNIQUES FOR DETECTING ACCESS RECIRCULATION

(71) Applicant: Fresenius Medical Care Holdings, Inc., Waltham, MA (US)

(72) Inventors: Vaibhav Maheshwari, Jersey City, NJ (US); Peter Kotanko, New York, NY (US); Stephan Thijssen, New York, NY (US)

(73) Assignee: Fresenius Medical Care Holdings, Inc., Walthamn, MA (US)

( * ) Notice: Subject to any disclaimer, the term of this patent is extended or adjusted under 35 U.S.C. 154(b) by 176 days.

(21) Appl. No.: 16/162,216

(22) Filed: Oct. 16, 2018

(65) Prior Publication Data
US 2019/0111200 A1    Apr. 18, 2019

Related U.S. Application Data

(60) Provisional application No. 62/573,583, filed on Oct. 17, 2017.

(51) Int. Cl.
*A61M 1/16* (2006.01)
*A61M 1/36* (2006.01)

(52) U.S. Cl.
CPC ........ *A61M 1/1613* (2014.02); *A61M 1/1694* (2013.01); *A61M 1/3609* (2014.02); *A61M 1/3658* (2014.02); *A61M 2205/3306* (2013.01); *A61M 2205/75* (2013.01); *A61M 2230/207* (2013.01)

(58) Field of Classification Search
CPC .............. A61M 1/1613; A61M 1/1694; A61M 1/3609; A61M 1/3658; A61M 2205/3306; A61M 2205/75; A61M 2230/207
See application file for complete search history.

(56) References Cited

U.S. PATENT DOCUMENTS

| | | | |
|---|---|---|---|
| 6,582,656 B1 | 6/2003 | Steuer et al. | |
| 2002/0062098 A1 | 5/2002 | Cavicchioli et al. | |
| 2008/0015487 A1* | 1/2008 | Szamosfalvi | A61M 1/3658 604/6.07 |

FOREIGN PATENT DOCUMENTS

| | | |
|---|---|---|
| EP | 1154809 A1 | 11/2001 |
| WO | 9819592 A1 | 5/1998 |

OTHER PUBLICATIONS

International Search Report and Written Opinion for application No. PCT/US2018/056139, dated Jan. 28, 2019, 11 pages.

* cited by examiner

*Primary Examiner* — Dirk R Bass
(74) *Attorney, Agent, or Firm* — Kacvinsky Daisak Bluni, PLLC

(57) ABSTRACT

Techniques and apparatuses for access recirculation of a patient during dialysis treatment are described. In one embodiment, for example, an apparatus may include at least one memory, and logic coupled to the at least one memory. The logic may be configured to determine a first hemoglobin concentration for a dialysis system, determine a change in an ultrafiltration rate, determine a second hemoglobin concentration modified due to the change in the ultrafiltration rate based on a dialysis system model of the dialysis system, and determine an access recirculation value for the dialysis system. Other embodiments are described.

20 Claims, 16 Drawing Sheets

$$550 \quad \frac{d(C_a V_a)}{dt} = Q_x C_x - (1-AR)Q_b C_a - (Q_x - (1-AR)Q_b)C_{af}$$

$$552 \quad \frac{d(C_{af} V_{af})}{dt} = (1-AR)Q_b C_a + AR \cdot Q_b C_w - Q_b C_{af}$$

$$554 \quad \frac{d(C_d V_d)}{dt} = Q_b C_{af} - (Q_b - Q_{wf})C_d$$

$$556 \quad \frac{d(C_w V_w)}{dt} = (Q_b - Q_{wf})C_d - AR \cdot Q_b C_w - (Q_b - Q_{wf} - AR \cdot Q_b)C_w$$

$$558 \quad \frac{d(C_x V_x)}{dt} = (Q_x - (1-AR)Q_b)C_{af} + (Q_b - Q_{wf} - AR \cdot Q_b)C_w - (Q_x - Q_{wf})C_x$$

FIG. 5B

$$\left.\begin{array}{l} 560 \quad C_a(t=0) \\ 562 \quad C_{af}(t=0) \\ 564 \quad C_d(t=0) \\ 566 \quad C_w(t=0) \\ 568 \quad C_x(t=0) \end{array}\right\} = 10\,g/dL$$

FIG. 5C

650 $\quad \dfrac{d(C_a V_a)}{dt} = Q_s C_v - (1-AR)Q_b C_a - (Q_s - (1-AR)Q_b)C_a,$ 652 $\quad \dfrac{\partial C_{at}}{\partial t} = -\dfrac{Q_b}{A_{tube}} \dfrac{\partial C_{at}}{\partial x},$ 654 $\quad \dfrac{\partial C_d}{\partial t} = -\dfrac{1}{NA} \dfrac{\partial}{\partial x}(QC_d),$ 656 $\quad \dfrac{\partial C_{vt}}{\partial t} = -\dfrac{Q_b - Q_{uf}}{A_{tube}} \dfrac{\partial C_{vt}}{\partial x},$ 658 $\quad \dfrac{d(C_v V_v)}{dt} = (Q_s - (1-AR)Q_b)C_a + (Q_b - Q_{uf} - AR\cdot Q_b)C_{vt} - (Q_s - Q_{uf})C_v$

*FIG. 6B*

660 
$$Q_b(x) = Q_{b,in} - \dfrac{x}{L_{dia}} Q_{uf},$$

$$Q_d(x) = Q_{d,in} + \dfrac{L_{dia} - x}{L_{dia}} Q_{uf}$$

*FIG. 6C*

672 
674 — Arterial access compartment: $C_a(t=0) = 10\,g/dL$
— Arterial tube segment: $C_{at}(x, t=0) = 10\,g/dL,$ $$C_{at}(x=0, t) = \dfrac{(1-AR)Q_b C_a + AR\cdot Q_b C_{vt}}{Q_b}$$

676 — Dialyzer fiber: $C_d(x, t=0) = 10\,g/dL$ $C_d(x=0, t) = C_{at}(x = L_{tube}, t)$ 678 — Venous tube segment: $C_{vt}(x, t=0) = 10\,g/dL$ $C_{vt}(x=0, t) = C_d(x = L_{fiber}, t)$ 680 — Venous access compartment: $C_v(t=0) = 10\,g/dL$

*FIG. 6D*

TECHNIQUES FOR DETECTING ACCESS RECIRCULATION

CROSS-REFERENCE TO RELATED APPLICATION

This application claims priority to U.S. Provisional Patent Application Ser. No. 62/573,583, filed on Oct. 17, 2017, entitled "Dialysis Access Recirculation," the contents of which are incorporated herein by reference.

TECHNICAL FIELD

Embodiments herein generally relate to processes and apparatuses operative to detect and/or measure access recirculation during dialysis treatment.

BACKGROUND

Circulatory system access is a fundamental requirement for extracorporeal renal replacement therapies, including dialysis treatment. Hemodialysis (HD) patients may use a hemodialysis catheter or, for long-term access, an arteriovenous (AV) fistula or graft configured to connect an artery to a vein for receiving dialysis treatment.

During dialysis, blood flows out of the patient at a certain blood flow rate (for instance, 300-500 mL/min). Since it comes from arterial access, this blood may generally be referred to as arterial blood. The toxin-laden arterial blood may be passed through a dialyzer for the removal of toxins and fluid to generate clean blood. After passing through the dialyzer, the clean blood may be returned to the patient via a venous access as venous blood. Typically, the venous blood should mix with systemic circulation. However, access recirculation (AR) may occur when dialyzed blood returning through the venous access reenters the extracorporeal circuit through the arterial access, rather than returning to the systemic circulation. Accordingly, a portion of the arterial blood flowing to the dialyzer may actually be clean venous blood. The mixing of arterial blood and venous blood may lead to a reduction of toxin concentration in the arterial blood flowing to the dialyzer, which may reduce the efficiency of dialysis.

Access complications may be a cause of AR. For example, AR may occur under conditions of low access flow, nearness of the arterial access to the venous access, and inadequate blood flow (for example, lower than the flow set on a dialysis blood pump). A common cause of low access flow is arterial and/or venous stenosis, which may restrict venous outflow and lead to a backlow in the arterial access. Accordingly, it is important to detect the presence of stenosis to meet dialysis adequacy goals. In addition, the presence of stenosis should be detected immediately because this condition may also lead to the malfunction of the access, such as a fistula. For example, if stenosis is detected early, a vascular surgeon may attempt to clear the stenosis and save the fistula.

Accordingly, accurate and efficient detection and/or measurement of AR during dialysis may facilitate safe dialysis treatment and patient health. It is with these considerations in mind that the present disclosure may be useful.

SUMMARY

In accordance with various aspects of the described embodiments is an apparatus that may include at least one memory and logic coupled to the at least one memory, the logic may determine a first hemoglobin concentration for a dialysis system, determine a change in an ultrafiltration rate, determine a second hemoglobin concentration modified due to the change in the ultrafiltration rate based on a dialysis system model of the dialysis system, and determine an access recirculation value for the dialysis system. In some embodiments, the change in the ultrafiltration rate may be a change from a known first ultrafiltration rate to a known second ultrafiltration rate. In various embodiments, the second ultrafiltration rate may be higher than the first ultrafiltration rate.

In some embodiments of the apparatus, the apparatus may further include a hematocrit measurement device. In some embodiments of the apparatus, the hematocrit measurement device may include an inline monitor operative to measure hematocrit during dialysis treatment by the dialysis system. In various embodiments of the apparatus, the hemoglobin concentration may be determined based on hematocrit measurement information determined by the hematocrit measurement device. In some embodiments of the apparatus, the dialysis system model may include one of a compartmental model and a tubular model. In exemplary embodiments of the apparatus, the dialysis system model may include an arterial access element, an arterial tube element, a hematocrit measurement device element, a dialyzer element, a venous tube element, and a venous access element. In some embodiments of the apparatus, the dialysis system model may include a tubular model comprising an arterial tube element, a dialyzer element, and a venous tube element configured or modeled as a tubular flow system. In various embodiments of the apparatus, the logic may operate to determine the access recirculation value based on at least one mass balance process of the dialysis system model.

In accordance with various aspects of the described embodiments is a method that may include determining a first hemoglobin concentration for a dialysis system, determining a change in an ultrafiltration rate, determining a second hemoglobin concentration modified due to the change in the ultrafiltration rate based on a dialysis system model of the dialysis system, and determining an access recirculation value for the dialysis system.

Some embodiments of the method may further include measuring hematocrit via a hematocrit measurement device. In exemplary embodiments of the method, the hematocrit measurement device may include an inline monitor operative to measure hematocrit during dialysis treatment by the dialysis system. In various embodiments of the method, the hemoglobin concentration may be determined based on hematocrit measurement information determined by the hematocrit measurement device. In some embodiments of the method, the dialysis system model may include one of a compartmental model and a tubular model. In various embodiments of the method, the dialysis system model may include an arterial access element, an arterial tube element, a hematocrit measurement device element, a dialyzer element, a venous tube element, and a venous access element. In some embodiments of the method, the dialysis system model may include a tubular model comprising an arterial tube element, a dialyzer element, and a venous tube element as a tubular flow system. In exemplary embodiments of the method, the method may include determining the access recirculation value based on at least one mass balance process of the dialysis system model.

BRIEF DESCRIPTION OF THE DRAWINGS

FIG. 5B illustrates mass balance processes for elements of the fifth operating environment according to an embodiment.

FIG. 5C illustrates initial states for elements of the fifth operating environment according to an embodiment.

FIG. 6B illustrates mass balance processes for elements of the sixth operating environment according to an embodiment.

FIG. 6C illustrates a process for changing the blood flow rate for the sixth operating environment according to an embodiment.

FIG. 6D illustrates initial states and boundary conditions for elements of the sixth operating environment according to an embodiment.

DETAILED DESCRIPTION

Figure 1:
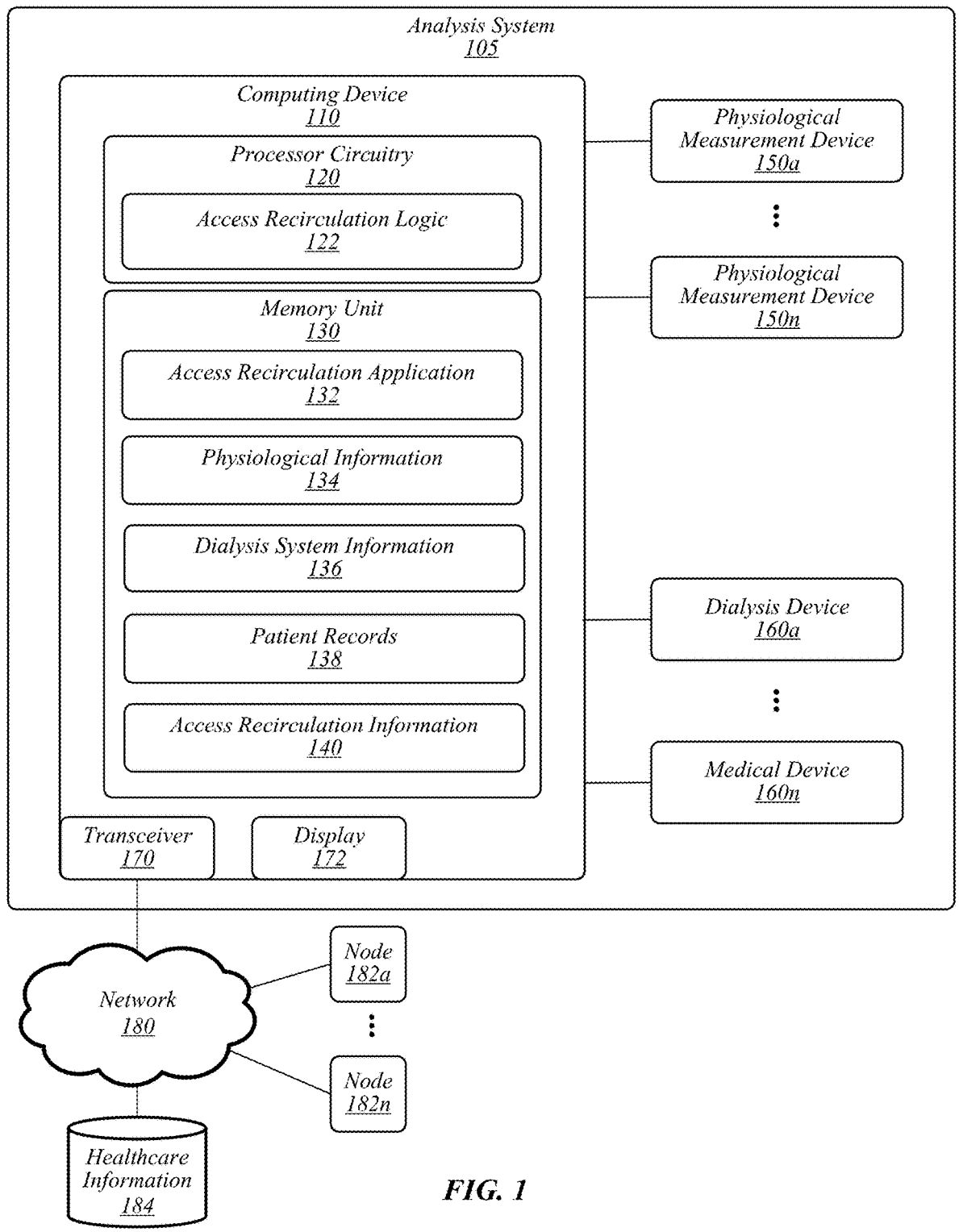
FIG. 1 illustrates an embodiment of a first operating environment.

Various embodiments may generally be directed toward systems, methods, and/or apparatus for determining access recirculation (AR) in patients undergoing dialysis treatment. In some embodiments, physiological information of a patient and dialysis system information may be measured or otherwise determined before, during, and/or after dialysis treatment. Non-limiting examples of physiological information may include hematocrit, oxygen saturation, hemoglobin concentration, and/or the like. Dialysis system information may include, without limitation, filtration rates (for instance, an ultrafiltration rate (UFR)), dialysis device dimensions (for instance, dialyzer fiber length, radius, and/or the like), patient characteristics, patient access site characteristics, venous access compartment volume, venous tube compartment volume, arterial access compartment volume, arterial tube compartment volume, dialyzer compartment volume, and/or the like. In various embodiments, an AR measurement process may use the physiological information and the dialysis system information to determine AR for a patient. In some embodiments, the access may be or may include an arterio-venous fistula (AVF).

Hematocrit, the ratio of the volume of red blood cells to the total volume of blood, may be measured during dialysis treatment. For example, blood (for instance, from extracorporeal and/or other sources) can be measured to determine the percentage change in blood volume using a blood volume (BV) device and/or a hematocrit measuring device such as a Crit-Line® Monitor (CLM), available from Fresenius Medical Care Waltham, Mass., United States of America. In general, a CLM may be an inline monitor operative to measure hematocrit, oxygen saturation, and/or changes in blood volume during dialysis treatment. Although a CLM may be used in some examples, embodiments are not so limited, as any technique, device, apparatus, system, process, and/or the like for measuring and/or predicting hematocrit capable of operating according to some embodiments is contemplated herein. In some embodiments, AR processes may be operative to measure AR based on measurements of solutes with no, substantially no, or minor dialytic removal and to provide ultrafiltration (UFR)-induced hemoconcentration measurement in real time, for instance, in the extracorporeal circuit (for example, hematocrit, hemoglobin, blood protein, and/or the like).

In various embodiments, hemoglobin concentration of a patient undergoing dialysis treatment may be measured directly by a hemoglobin concentration measurement device. In some embodiments, hemoglobin concentration may be determined from measured hematocrit values. For example, hemoglobin concentration (for instance, in units of g/dL) may be equal to hematocrit (% packed cell volume (PCV))×about 0.3 (for instance, 0.34). In another example, hemoglobin concentration (for instance, in units of g/dL) may be equal to hematocrit (decimal fraction)×about 30 (for instance, 34). Other methods and/or values for determining hemoglobin concentration from hematocrit may also be used. Embodiments are not limited in this context.

For example, in some embodiments, hematocrit and oxygen saturation in the arterial blood of a patient may be measured before, during, and/or after dialysis treatment. Since hematocrit does not diffuse through the dialyzer membrane and fluid is removed along the fiber due to UFR, the hematocrit at dialyzer exit, for instance, in venous blood may be higher than that in arterial blood. The presence of AR may lead to mixing of this venous blood with arterial blood, and thus increased hematocrit. Accordingly, the measured hematocrit may be hematocrit in arterial blood mixed with some venous blood. Measured hematocrit may increase with increased UFR, for example, in the presence of AR. This perturbation in UFR may be used to detect and/or measure AR according to some embodiments. For example, the hematocrit measured by the CLM may actually be hematocrit in the arterial blood mixed with a portion of venous blood. If UFR is increased, the hematocrit in the venous line will increase and, in the presence of AR, also the hematocrit measured by the CLM. This perturbation in UFR can assist in measuring the AR according to some embodiments.

In various embodiments, an AR measurement process may be used to, among other things, quantify a change in hematocrit due to a change (or perturbation) in UFR and/or determine a period of time to detect an expected change in hematocrit. In some embodiments, the AR measurement process may use hemoglobin concentration, for example, that is calculated from a hematocrit measurement. In various embodiments, the AR measurement process may model and/or quantify the change in hematocrit due to change in UFR and the period of time to see the change in hematocrit.

Conventional techniques for measuring AR may include urea-based methods, ultrasound dilution methods, saline infusion methods, conductivity methods, blood temperature monitor methods, and/or the like. AR measurement processes according to some embodiments may provide technological advantages over conventional methods by detecting and/or determining AR based on hematocrit measurements. For example, in various embodiments, AR measurement processes may provide technological advantages and/or improvements in computing technology by detecting and/or determining AR based on hematocrit measurements by, inter alia, determining a change in hematocrit due to a change (or perturbation) in UFR as well as the period of time to see the change in hematocrit. In addition, processes according to some embodiments may detect, measure, determine, and/or predict AR non-invasively and, in systems using a hematocrit measurement device (for instance, a CLM), without substantial increased costs.

Some embodiments may provide an AR measurement process configured according to various dialysis system configurations. Non-limiting examples of dialysis system configurations may include a compartmental configuration and a tubular configuration. Accordingly, AR measurement processes may include a compartmental model, technique, method, and/or other process (see, for example, FIG. 5A) and a tubular model, technique, method, and/or other process (see, for example, FIG. 6A). In various embodiments, AR processes may provide compartmental configuration and tubular configuration process and/or model approaches operative to quantify the change in hemoglobin concentration subjected to UFR perturbation, based on the particular characteristics of compartmental configurations and tubular configurations, respectively. Although a compartmental AR process and a tubular AR process are described in some examples, embodiments are not so limited, as other AR processes may be configured for different types of dialysis system configurations.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage physiological analysis, treatment, and/or the like of a patient. In various embodiments, analysis system 105 may include computing device 110 communicatively coupled to one or more physiological measurement devices 150a-n and/or medical devices 160a-n, or otherwise configured to receive and store data therefrom. For example, physiological measurement devices 150a-n and/or medical devices 160a-n may operate to provide data to a location on a network 150 (for instance, a cloud computing environment), such as nodes 182a-n, healthcare information database 184, and/or the like, accessible to computing device 110. In some embodiments, computing device 110 may be operative to control, monitor, manage, or otherwise process various operational aspects of physiological measurement devices 150a-n and/or medical devices 160a-n. In some embodiments, computing device 110 may be or may include a stand-alone computing device, such as a personal computer (PC), server, tablet computing device, cloud computing device, smartphone, tablet computing device, and/or the like. In some embodiments, computing device 110 may be an embedded computing device in one or more of physiological measurement devices 150a-n and/or medical devices 160a-n.

As shown in FIG. 1, computing device 110 may include processing circuitry 120, a memory unit 130, a transceiver 170, and/or a display 172. Processing circuitry 120 may be communicatively coupled to memory unit 130, transceiver 170, and/or display 172.

Figure 14:
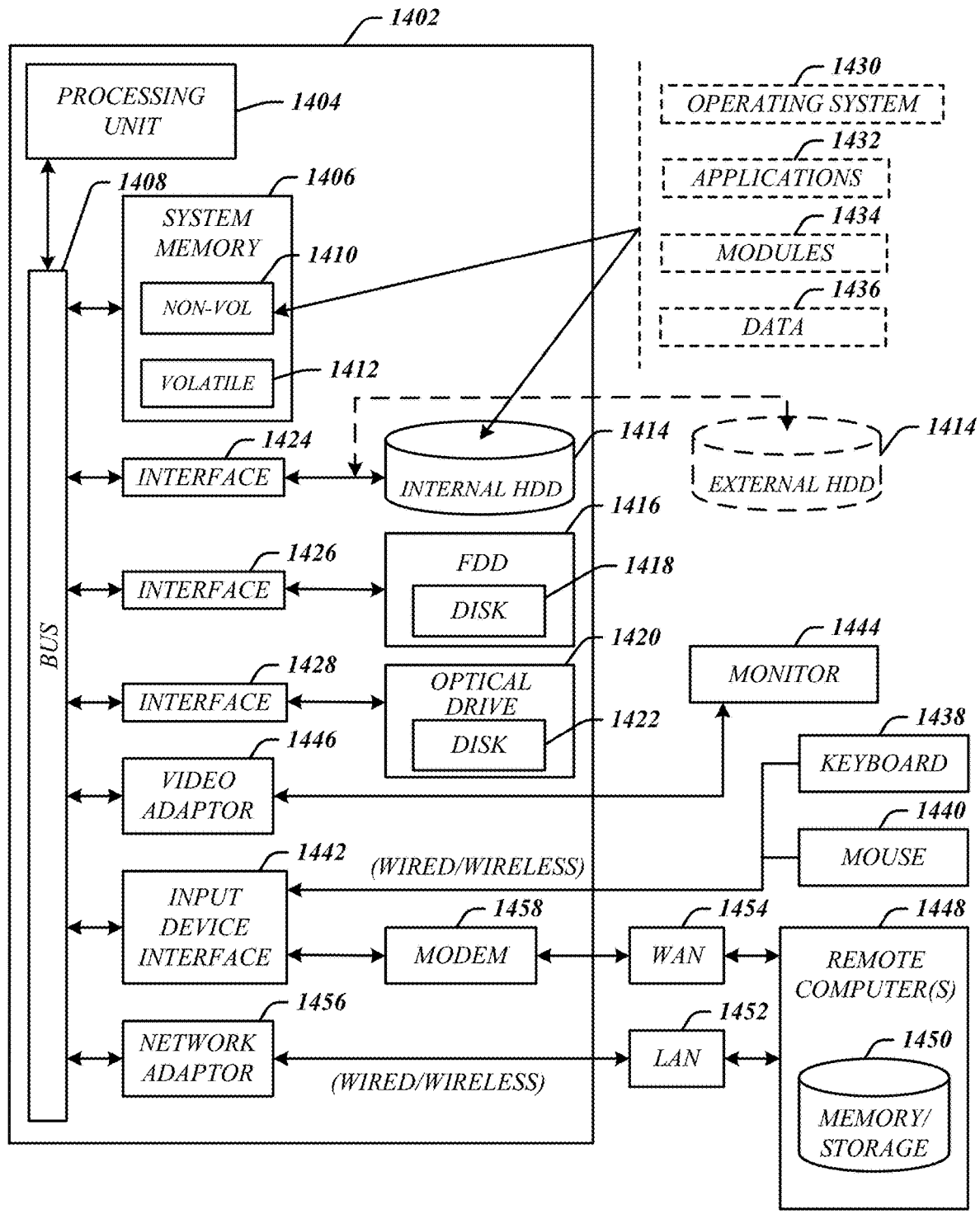
FIG. 14 illustrates an embodiment of a computing architecture.

Processing circuitry 120 may include and/or may access various logic for performing processes according to some embodiments. For instance, processing circuitry 120 may include and/or may access recirculation (or AR) logic 122. Processing circuitry and/or AR logic 122, or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1400 (FIG. 14). For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although AR logic 122 is depicted in FIG. 1 as being within processing circuitry 120, embodiments are not so limited. For example, AR logic 122 may be located within an accelerator, a processor core, an interface, an individual processor die, implemented entirely as a software application (for instance, access recirculation (or AR) application 132) and/or the like.

In some embodiments, physiological measurement devices 150a-n may include various devices operative to measure physiological characteristics of a patient. Non-limiting examples of physiological devices 150a-n may include a blood volume device, blood pressure device, an oxygen concentration measurement device, hematocrit measurement device (for instance, a CLM), hemoglobin measurement device, and/or the like. Although a hematocrit measurement device (for instance, a CLM) may be used as an illustrative physiological measurement device 150a-n, embodiments are not so limited, as physiological measurement devices 150a-n may include any type of device capable of measuring physiological information of a patient.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store an AR application 132 that may operate, alone or in combination with AR logic 122, to perform various functions for determining AR and/or performing AR measurement processes according to some embodiments. In some embodiments, AR application 132 may include application programming interfaces (APIs) and/or graphical user interfaces (GUIs) to read, write, and/or otherwise access physiological information 134, dialysis system information 136, and/or patient records 138, such as via display 172 and/or corresponding displays of physiological measurement devices 150a-n, medical devices 160a-n, nodes 182a-n, web interfaces, mobile application ("mobile applications," "mobile apps," or "apps"), and/or the like. In this manner, in some embodiments, an operator may search, visualize, read, add to, or otherwise access physiological data, patient records, and/or the like. In various embodiments, an operator may perform an analysis to determine hematocrit values, determine oxygen concentration values, determine AR measurements, operate physiological measurement devices 150a-n, medical devices 160a-n, and/or the like.

In various embodiments, physiological information 134 may include information used by AR application 132 to detect AR and/or determine AR measurements. Non-limiting examples of physiological information may include hematocrit, oxygen saturation, hemoglobin concentration, and/or the like. In some embodiments, dialysis system information may include physical information of dialysis device 160a and/or a patient (such as access elements) receiving dialysis treatment used by AR application 132 to detect AR and/or determine AR measurements. Dialysis system information may include, without limitation, filtration rates (for instance, an ultrafiltration rate (UFR)), dialysis device dimensions (for instance, dialyzer fiber length, radius, and/or the like), venous access compartment volume, venous tube compartment volume, arterial access compartment volume, arterial tube compartment volume, dialyzer compartment volume, and/or the like. Embodiments are not limited in this context. AR application 132 may use physiological information 132 and/or dialysis system information 136 to generate AR information 140. In various embodiments, AR information 140 may indicate the presence of AR and/or measurements of AR for a patient undergoing dialysis treatment (including associated time stamp or treatment segment information corresponding to the presence of AR and/or AR measurements).

In some embodiments, AR application 132 may analyze AR information 140 to determine whether a dialysis complication event has occurred. For example, a dialysis complication event may include an AR measurement above a threshold amount, an AR measurement associated with stenosis, and/or the like. In various embodiments, AR application 132 may include various thresholds, warning levels, alerts, and/or the like that may be configured by an operator. For example, AR application 132 may include an AR warning threshold, a stenosis threshold, and/or the like. In some embodiments, for example, if an AR value is determined for a patient over the AR warning threshold, a warning may be generated (for example, presented on display 172, a display of dialysis device 160a, a display of node 182a, and/or recorded in a corresponding patient record). In some embodiments, for example, if an AR value is determined for a patient over the stenosis threshold, a warning or other message may be generated indicating that a stenosis condition may be present. In various embodiments, if an AR value is measured above an AR threshold, dialysis device 160a may generate a warning and/or stop performing dialysis. Embodiments are not limited in this context.

In some embodiments, access recirculation application 132 may read, write, create, or otherwise access patient records 138. In various embodiments, patient records 138 may be stored in healthcare information database 184, which may be or may include a hospital information management system (HIMS), laboratory information management system (LIMS), Health Information System (HIS), electronic medical records (EMR), and/or the like. In some embodiments, for example, physiological information 134, dialysis information, AR values, AR warnings, and/or the like, may be written into patient records 138 before, during, and/or after dialysis treatment.

Figure 2:
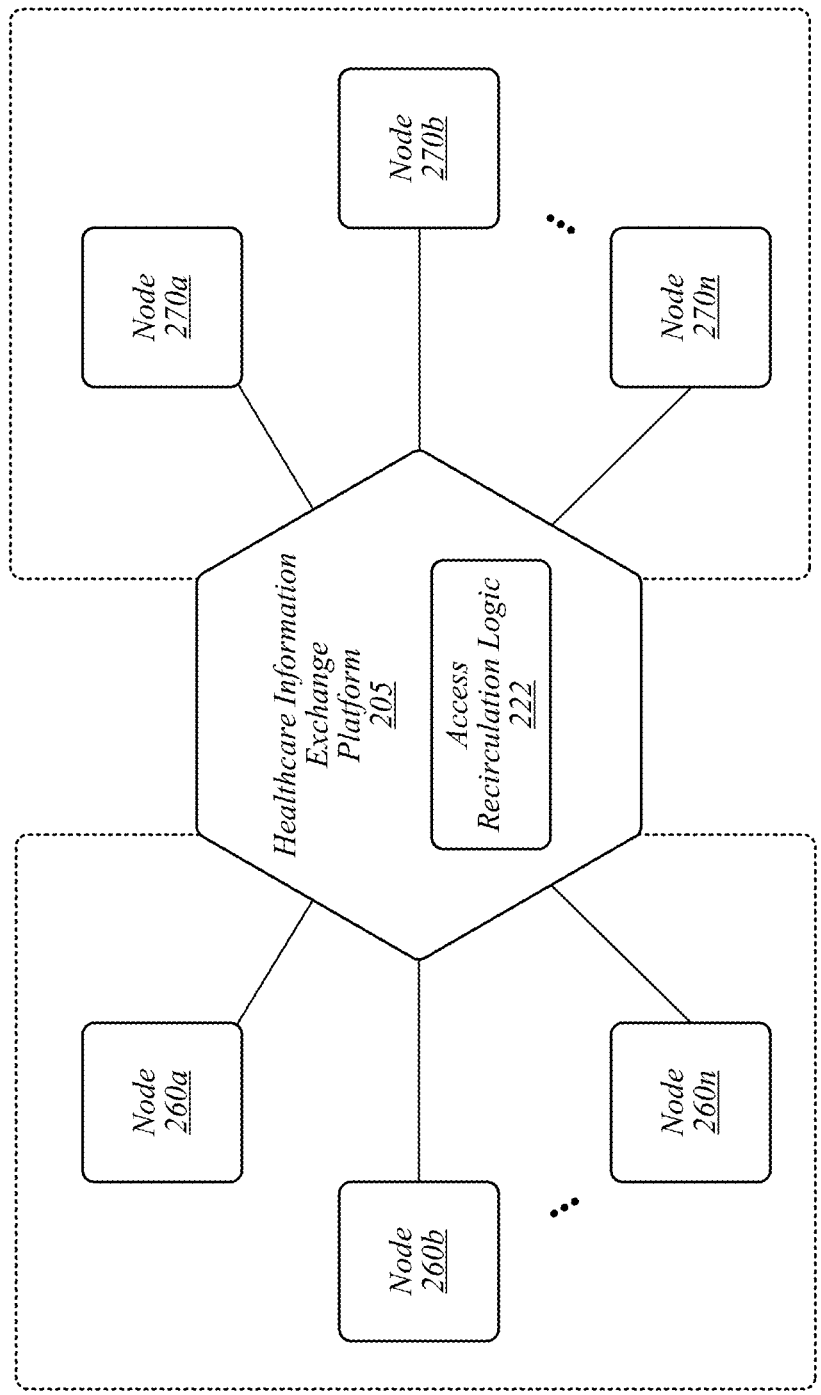
FIG. 2 illustrates an embodiment of a second operating environment.

FIG. 2 illustrates an example of an operating environment 200 that may be representative of some embodiments. As shown in FIG. 2, operating environment 200 may include an healthcare information exchange platform (or a medical device platform) 205. In some embodiments, healthcare information exchange platform 205 may be operative to provide for the exchange of healthcare information among interested entities. In various embodiments, healthcare information exchange platform 205 may include an application platform operative to provide data exchange services among nodes 260a-n and 270a-n. In exemplary embodiments, healthcare information exchange platform 205 may be a software platform, suite, set of protocols, and/or the like provided to customers by a manufacturer and/or developer ("developer") associated with medical devices, medical care services, clinical research services, laboratory services, and/or the like.

For example, a developer may provide healthcare information exchange platform 205 as a data exchange interface for medical devices and/or medical device services. For example, one or more of nodes 270a-n may include a dialysis medical device or system. An entity, such as a hospital, dialysis clinic, or other healthcare provider providing services to patients using a medical device node 270a-n provided by developer may use healthcare information exchange platform 205 to implement processes according to some embodiments, such as dialysis complication monitoring via AR logic 222. Other entities, may access healthcare information exchange platform 205 via a GUI, such as a client application, web interface, mobile app, and/or the like, to perform functions associated with AR logic 222. In some embodiments, at least a portion of healthcare information exchange platform 205 may be hosted in a cloud computing environment.

Nodes 270a-n may be data producers for AR logic 222 and nodes 260a-n may be data consumers of AR logic 222. For example, node 270a-n may include dialysis devices, blood pressure devices, hematocrit measurement devices (for instance, a CLM), oxygen concentration measurement devices, and/or other data producers. Nodes 260a-n may include third-party applications, decision makers, analysis processes, regulators, and/or other data consumers. An entity may be both a data producer and a data consumer.

For example, nodes 270a and 270b may be a CLM (or other hematocrit measurement device) and a dialyzer operative to function according to some embodiments. Data generated by node 270a and/or 270b may be provided to AR logic 222 for processing, for example, such as hematocrit information, UFR information, and/or the like. AR logic 222 may use the information from nodes 270a and/or 270b to generate AR information. The AR information may be provided to one or more of nodes 260a-n, such as a hospital, HIMS, HIS, LIS, EMR, and/or the like. For example, the AR information may be used by a hospital, clinic, dialysis center, or doctor's office to treat a patient, such as determining operating parameters for a dialysis machine and/or monitoring for dialysis complications (for instance, stenosis). In another example, the AR information may be used by a clinical researcher to evaluate dialysis procedures performed in a clinic. Embodiments are not limited in this context.

In some embodiments, healthcare information exchange platform 205 may operate according to a cloud-based model and/or an "as-a-Service" model. In this manner, healthcare information exchange platform 205 may provide for a service that operates as a single, central platform that allows entities to access physiological information, dialysis system information, AR information, and/or the like to perform healthcare services, research, and/or the like.

Figure 3:
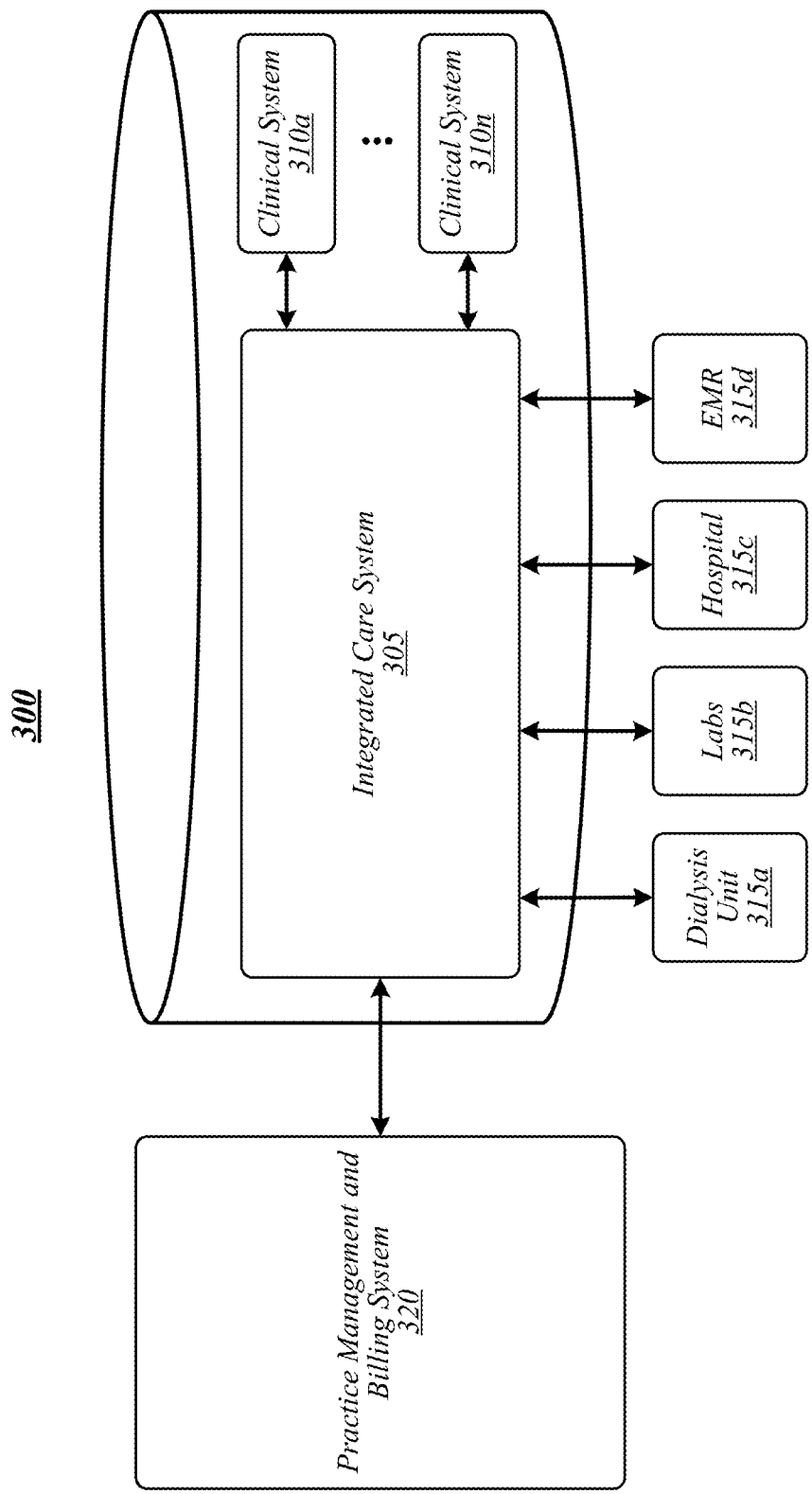
FIG. 3 illustrates an embodiment of a third operating environment.
Figure 4:
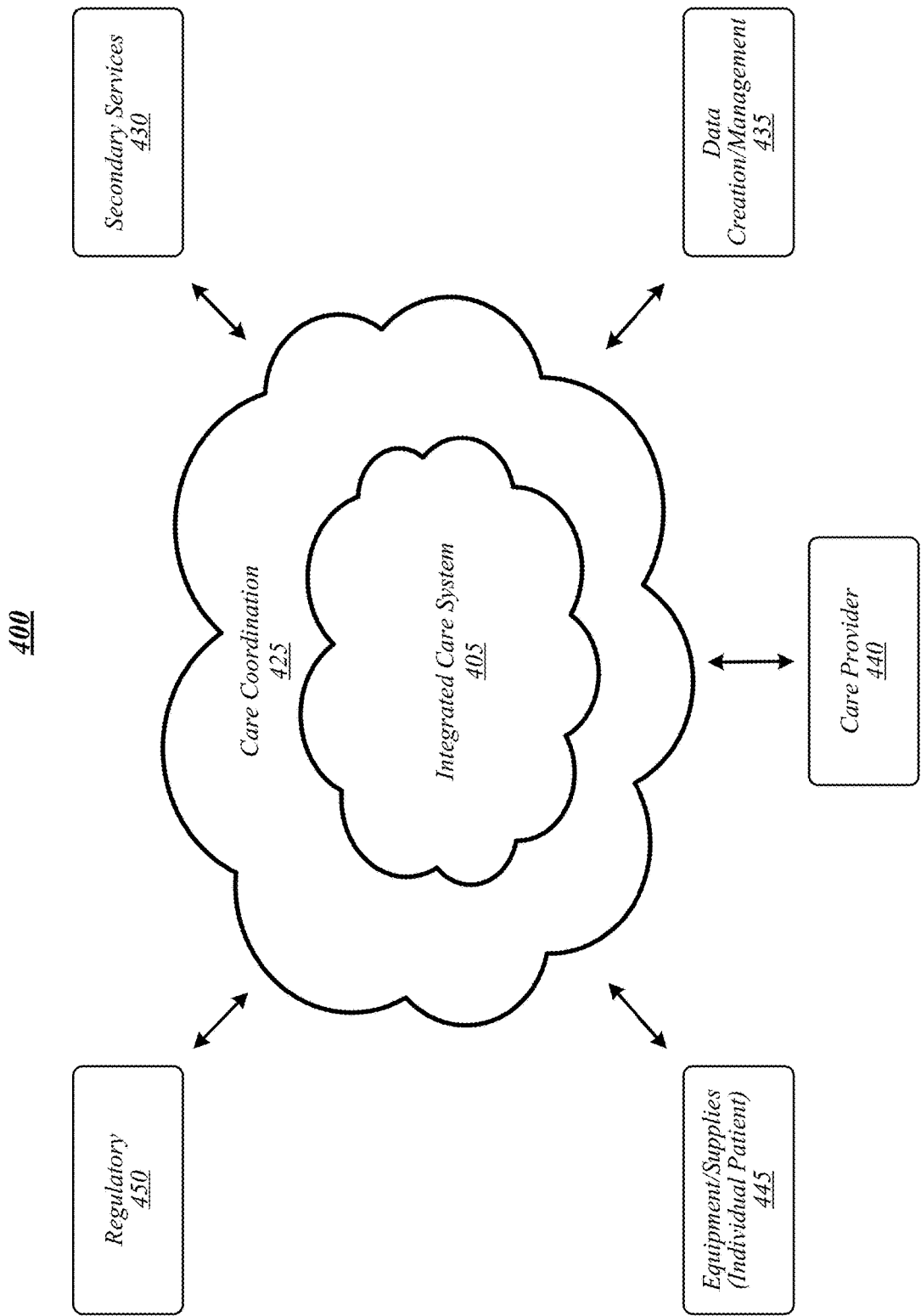
FIG. 4 illustrates an embodiment of a fourth operating environment.

FIG. 3 illustrates an example of an operating environment 300 that may be representative of some embodiments. As shown in FIG. 3, operating environment 300 may include an integrated care system 305 that may form a part of a clinical system for treating a patient in all aspects of care. In some embodiments, integrated care system 305 may include a specific implementation of healthcare information exchange platform 205.

Integrated care system 305 may be connectable to additional clinical systems 310a-n, including but not limited to a pharmacy, an End-Stage Renal Disease (ESRD) and/or Chronic Kidney Disease (CKD) data registry, a hospital, a dialysis clinic, a renal and/or kidney disease research facility, and/or the like. For example, integrated care system 305 may automatically send prescriptions and other patient information to a pharmacy based on information provided by a medical professional, and may be able to send and receive data and information to the CKD/ESRD data registry, for comparison to other patients and projections for future treatment. In another example, integrated care system 305 may determine and/or access AR information. Integrated care system 305 may determine events associated with CKD/ESRD and take appropriate action, including but not limited to informing patients, informing clinicians of when specific interventions are warranted, and/or alerting clinicians to upcoming important dates for interventions.

One or more outside systems 315a-d may also be connectable to integrated care system 305. For example, the outside systems 315a-d may include one or more of a dialysis unit (or dialysis machine) 315a, labs 315b, doctor's office and/or hospital 315c, and/or electronic medical records (EMR) 315d. Patient information, including physiological information, dialysis system information, and/or AR information, may be sent and received between integrated care system 305 and the outside systems 315a-n, so that patient care and/or research may be more efficient, standardized, and consistent across several functions. For example, integrated care system 305 may receive information from a patient's electronic medical records, thereby accessing historical information. Dialysis unit 315a, labs 315b, doctor's office or hospital 315c, EMR 315d, and/or the like may send and receive information to and from integrated care system 305 based on patient treatment.

Figure 12:
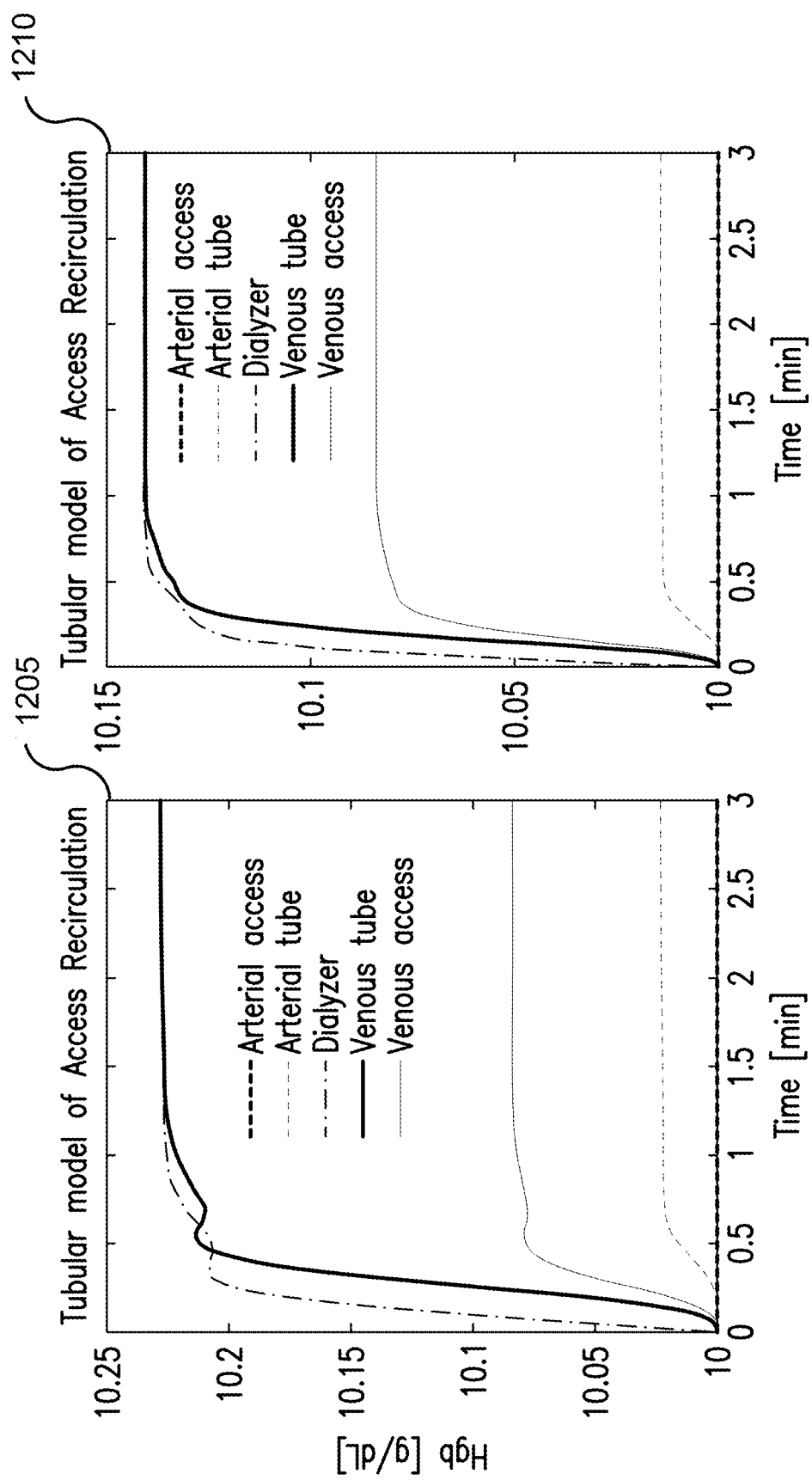
FIG. 12 illustrates graphs of model output for a tubular model according to an embodiment.

As described below with respect to FIG. 12, in some embodiments, integrated care system 305 may provide information to a dialysis machine 1300 for use in dialysis treatment. In some embodiments, integrated care system 305 may send the dialysis machine 1300 a prescription from a medical professional for a prescribed dialysis treatment, in which case integrated care system 305 may receive the prescription from a doctor's office or hospital (in some embodiments, the prescription may include a UFR). Integrated care system 305 may also be able to verify the prescribed treatment against the patient's lab work or medical records. In some embodiments, integrated care system 305 may determine and/or obtain, such as from labs 315b, EMR 315d, and/or the like, AR information determined according to various embodiments for a patient. In exemplary embodiments, integrated care system 305 may remotely program the prescription and/or AR information onto the patient's dialysis machine and/or forward the prescription and/or AR information to the machine for local set-up. In this manner, the patient may be sure to receive the necessary and correct treatment and may be prevented from administering or receiving an improper amount of dialysis treatment, thereby reducing human error and improving patient care.

Integrated care system 305 may also be able to inform the relevant medical professional based on information received from these outside systems 315a-n, as well as the additional clinical systems 310a-n, to provide appropriate medical treatment to the patient, including course(s) of treatment that may lessen or avoid a risk of hospitalization. For instance, AR information determined according to some embodiments may be used to inform the relevant medical professional of a dialysis complication condition, such as stenosis of a dialysis access site.

Figure 5A:
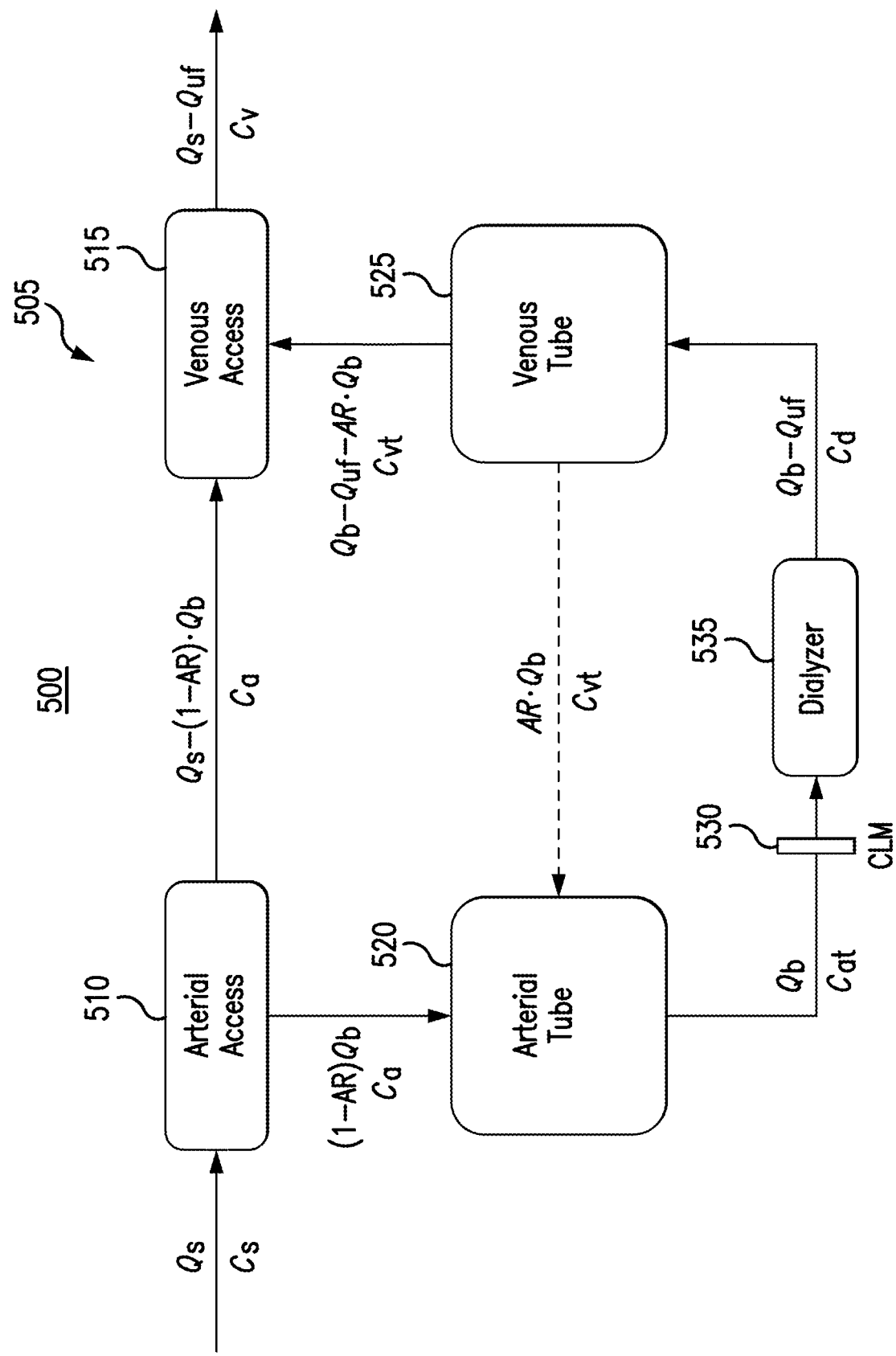
FIG. 5A illustrates an embodiment of a fifth operating environment.

FIG. 5A illustrates an example of an operating environment 500 that may be representative of some embodiments. As shown in FIG. 5A, operating environment 500 may include a compartmental dialysis system 505 structured according to a compartmental model. In various embodiments, compartmental dialysis system 505 may include an arteriovenous access (fistula or graft) configured, for example, as a tubular structure. In some embodiments, compartment dialysis system 505 may include an arterial access 510, a venous access 515, an arterial tube 520, a venous tube 525, a hematocrit measurement device (for instance, a CLM) 530, and a dialyzer 535. Flow streams and associated hemoglobin (Hgb) concentrations are depicted for the segments of the compartmental dialysis system (see TABLE 1 for nomenclature). In various embodiments, a compartmental AR process may assume that at least a portion of venous tube output mixes with arterial tube blood (aligning, for example, with an AR determination based on urea-based measurements).

The following TABLE 1 provides nomenclature used in this Detailed Description to describe AR processes and associated elements and/or characteristics thereof according to some embodiments:

TABLE 1

| Symbol | Description | Value | Unit |
| --- | --- | --- | --- |
| AR | Access recirculation (portion of blood flow coming from venous tube and mixing with arterial tube), | 0.1 | — |
| $C_a$ | Concentration in arterial access compartment | — | g/dL |
| $C_{at}/C_{at}(x, t)$ | Concentration in arterial tube compartment/arterial tube segment at position x and at time t | — | g/dL |
| $C_d/C_d(x, t)$ | Concentration in dialyzer compartment/dialyzer fiber segment at position x and at time t | — | g/dL |
| $C_v$ | Concentration in venous access compartment | — | g/dL |
| $C_{vt}/C_{vt}(x, t)$ | Concentration in venous tube compartment/venous tube segment at position x and at time t | — | g/dL |
| $C_s$ | Systemic concentration of hemoglobin | 10 | g/dL |
| $L_{fiber}$ | Length of dialyzer fiber | 23 | cm |
| $L_{tube}$ | Equivalent length of arterial/venous tube (calculated) | 598 | cm |
| N | Number of fibers in dialyzer casing (calculated) | 12553 | — |
| $R_{fiber}$ | Inner radius of a fiber | 105 | μm |
| $R_{tube}$ | Inner radius of arterial/venous tube segment | 2 | mm |
| $Q_b$ | Blood flow in dialyzer | 300-500 | mL/min |
| $Q_s$ | Systemic blood flow rate in access | 1200 | mL/min |
| $Q_{uf}$ | Ultrafiltration rate | 10 | mL/min |
| $V_a$ | Volume of arterial access compartment | 5 | mL |
| $V_{at}$ | Volume of arterial tube compartment | 75 | mL |
| $V_d$ | Volume of dialyzer compartment | 100 | mL |
| $V_v$ | Volume of venous access compartment | 5 | mL |
| $V_{vt}$ | Volume of venous tube compartment | 75 | mL |
| $A_{tube}$ | Area of tube | | |

Although certain symbols may have assigned values in TABLE 1, these values are for illustrative purposes only and embodiments are not so limited. For example, $C_s$ is indicated as having a value of 10 g/dL. However, $C_s$ may have a value of 1 g/dL, 2 g/dL, 5 g/dL, 10 g/dL, 20 g/dL, 30 g/dL and values and/or ranges between any two of these values (including endpoints). More specifically, the predetermined value of certain symbols may depend on the characteristics of a particular dialysis system. For instance, $C_s$, $L_{fiber}$, $L_{tube}$, N, $R_{fiber}$, $R_{tube}$, $Q_b$, $Q_s$, $Q_{uf}$, $V_a$, $V_{at}$, $V_d$, $V_v$, and/or $V_{vt}$ may depend on the particular characteristics of a dialysis system, patient, patient access site elements, and/or the like. In various embodiments, values for symbols, such as $C_s$, $L_{fiber}$, $L_{tube}$, N, $R_{fiber}$, $R_{tube}$, $Q_b$, $Q_s$, $Q_{uf}$, $V_a$, $V_{at}$, $V_d$, $V_v$, and/or $V_{vt}$ may have to be determined for each dialysis system, patient, patient access site, configuration thereof, and/or the like. Concentrations listed in TABLE 1 refer to hemoglobin concentrations.

In some embodiments, compartmental dialysis system 505 may have an approximate blood volume of 10 mL and may be approximated as two compartments, arterial access 510 and venous access 515, each with a volume of about 5 mL. From arterial access 505, a portion of blood goes in to arterial line or tube 520 (approximated according to some embodiments as a 75 mL compartment), and the rest may flow in fistula/graft. The output of arterial tube 520 compartment perfuses dialyzer 535 (approximated compartment volume of 100 mL). In dialyzer 535, fluid may be removed at a certain UFR. The output of dialyzer 535 may be fed into venous tube 525 (approximate compartment volume of 75 mL). The output of venous tube 535 may mix with fistula flow in venous access 515. The presence of AR may causes a portion of venous tube compartment 525 output to be redirected to arterial tube 520 compartment inlet. In some embodiments, AR may be defined as the fraction of arterial tube blood ($Q_b$) coming from venous tube 525, and it is assumed that AR·$Q_b$ comes from venous tube 525. In various embodiments, $Q_b$ may be blood flow driven by a pump (not shown), such that the output from arterial access 510 to arterial tube 520 is (1−AR)·$Q_b$.

Approximated values are for illustrative purposes only as some embodiments may include different values and/or approximated values based on the particular configuration of a dialysis system, patient, patient access elements, and/or the like. In various embodiments, a compartmental AR process may assume that all compartments are uniformly or substantially uniformly mixed and output concentration from a compartment is Hgb concentration inside the compartment; however, some embodiments may operate using some, all, or none of these assumptions.

Referring to FIG. 5B, therein is provided processes 550, 552, 554, 556, and 558 for determining the mass balance in each compartment. For example, process 550 determines the mass balance in arterial access 510, process 552 determines the mass balance in arterial tube 520, process 554 determines the mass balance in dialyzer 535, process 556 determines the mass balance in venous tube 525, process 558 determines the mass balance in venous access 515. Referring to FIG. 5C, therein is provided initial states 560, 562, 564, 566, and 568 for arterial access 510, arterial tube 520, dialyzer 535, venous tube 525, and venous access 515, respectively. In some embodiments, one or more AR values may be determined by solving or otherwise determining one or more mass balance processes 550, 552, 554, 556, and/or 558 for AR, for instance, based on assumed and/or measured values for concentration, flow, and/or the like. In some other embodiments, one or more AR values may be determined by estimating, predicting, assuming and/or the like AR values in one or more of mass balance processes 550, 552, 554, 556, and/or 558 and determining an AR value that corresponds with assumed and/or measured values for concentration, flow, and/or the like.

Figure 6A:
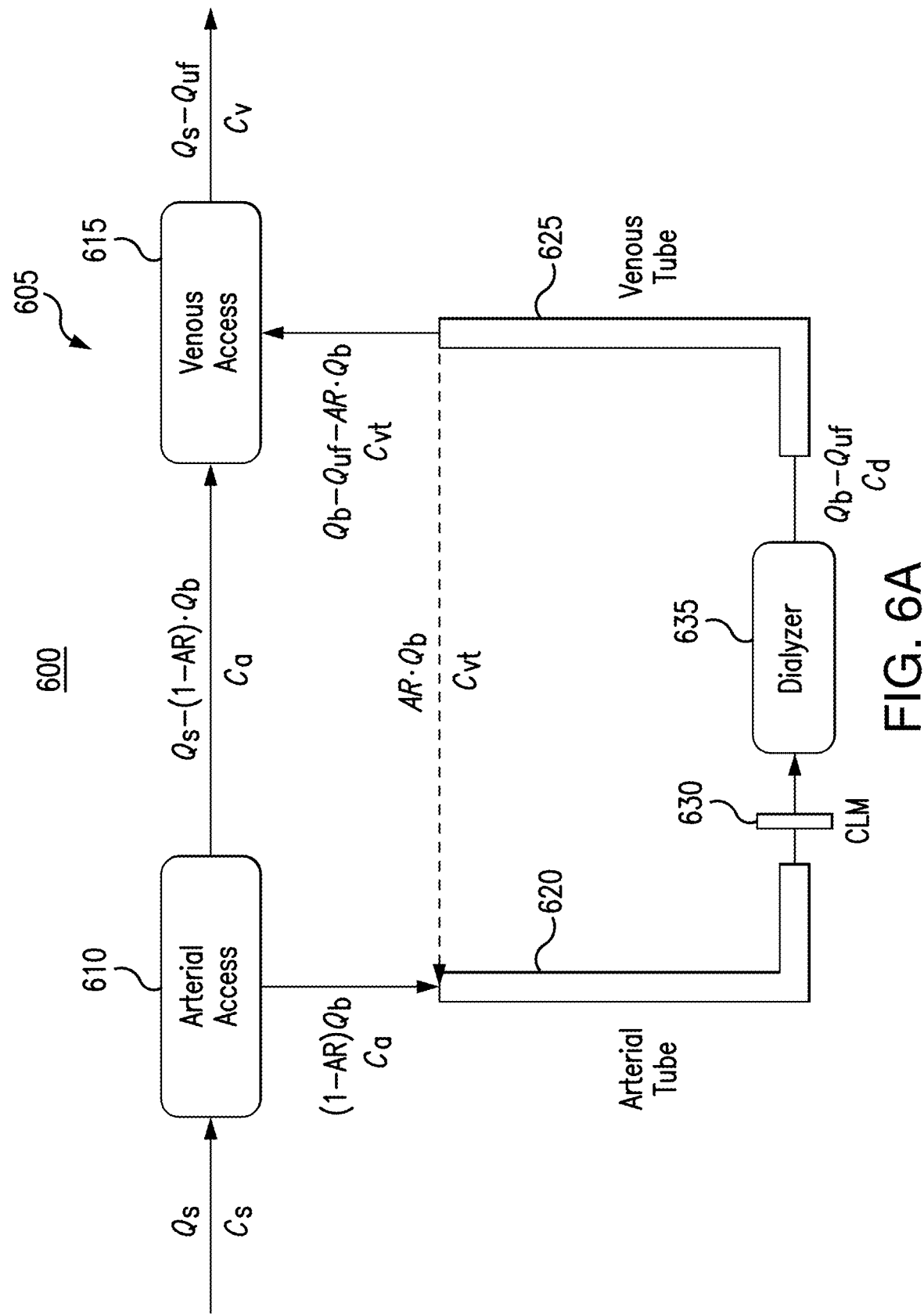
FIG. 6A illustrates an embodiment of a sixth operating environment.

FIG. 6A illustrates an example of an operating environment 600 that may be representative of some embodiments. As shown in FIG. 6A, operating environment 600 may include a tubular dialysis system 605 structured according to a tubular model. For example, tubular dialysis system 605 may include an extracorporeal circuit modeled as a tubular circuit that includes an arterial access 610, a venous access 615, an arterial tube 620, a venous tube 625, a hematocrit measurement device 630 (for instance, a CLM), and/or a dialyzer 635. Unlike compartmental dialysis system 505 of FIG. 5A, in tubular dialysis system 605, arterial tube 620, dialyzer 635, and venous tube 625 may be modeled as a tubular or plug flow system.

In some embodiments, arterial tube 620, dialyzer 635, and venous tube 625 volume may be approximated as 75 mL, 100 mL, and 75 mL, respectively. In various embodiments, the volume information may be used to determine arterial and/or venous tube length ($L_{tube}$) for a given tube radius $R_{tube}$ of 2 mm according to the following: $\pi(R_{tube})^2 L_{tube} = 75$ cm$^3$. The length in this example of arterial/venous tube ($L_{tube}$) will be 596.83 cm. Although such a tube length may seem very long, in a real extracorporeal circuit, the arterial/venous tube may contain an arterial/venous pressure chamber and/or a peristaltic pump tube segment, both with relatively large volume. In various embodiments, without modeling these different segments, models may approximate the total arterial/venous tube volume by uniform radius tube.

In exemplary embodiments, the priming volume of a dialyzer, such as dialyzer 635, may be approximated as 100 ml. This approximated priming volume may be used to calculate the total number of fibers in a dialyzer, such as dialyzer 635. This volume may correspond to the blood volume inside dialyzer fibers at any time point during dialysis. In some embodiments, the fiber length may be or may be approximated as 23 cm ($L_{fiber}$) and a fiber inner radius may be or may be approximated as $R_{fiber}$=105 µm. Accordingly, total fiber volume in this example may be determined according to the following: $N \cdot \pi (R_{fiber})^2 L_{fiber}$=100 cm³ for N=12,553.

Referring to FIG. 6B, therein is provided processes 650, 652, 654, 656, and 658 for determining the mass balance in each compartment. For example, process 650 determines the mass balance in arterial access 610, process 652 determines the mass balance in arterial tube 620, process 654 determines the mass balance in dialyzer 635, process 656 determines the mass balance in venous tube 625, process 658 determines the mass balance in venous access 615. In some embodiments, one or more AR values may be determined by solving or otherwise determining one or more mass balance processes 650, 652, 654, 656, and 658 for AR, for instance, based on assumed and/or measured values for concentration, flow, and/or the like. In some other embodiments, one or more AR values may be determined by estimating, predicting, assuming and/or the like AR values in one or more of mass balance processes 650, 652, 654, 656, and 658 and determining an AR value that corresponds with assumed and/or measured values for concentration, flow, and/or the like.

Referring to FIG. 6C, therein is provided a process 660 for changing the blood flow rate along the dialyzer fiber according to some embodiments. Referring to FIG. 6D, therein is provided initial states and/or boundary conditions 670, 672, 674, 676, and 678 for arterial access 610, arterial tube 620, dialyzer 635, venous tube 625, and venous access 615, respectively. In defining the tubular model boundary conditions, some embodiments may assume that at arterial tube 620 inlet, complete or substantially complete mixing may occur between the output of arterial access 610 compartment and venous tube 625 recirculation fraction. The Hgb concentration at arterial tube 620 inlet may be given in boundary condition 674. In some embodiments, a difference between the AR compartmental process (for instance, FIG. 5A) and the tubular AR process (for instance, FIG. 6A) is that homogenous concentration may not be used in the tubular AR process; rather, the concentration may vary along the length of the tube (for instance, between inlet and outlet).

Figure 7:
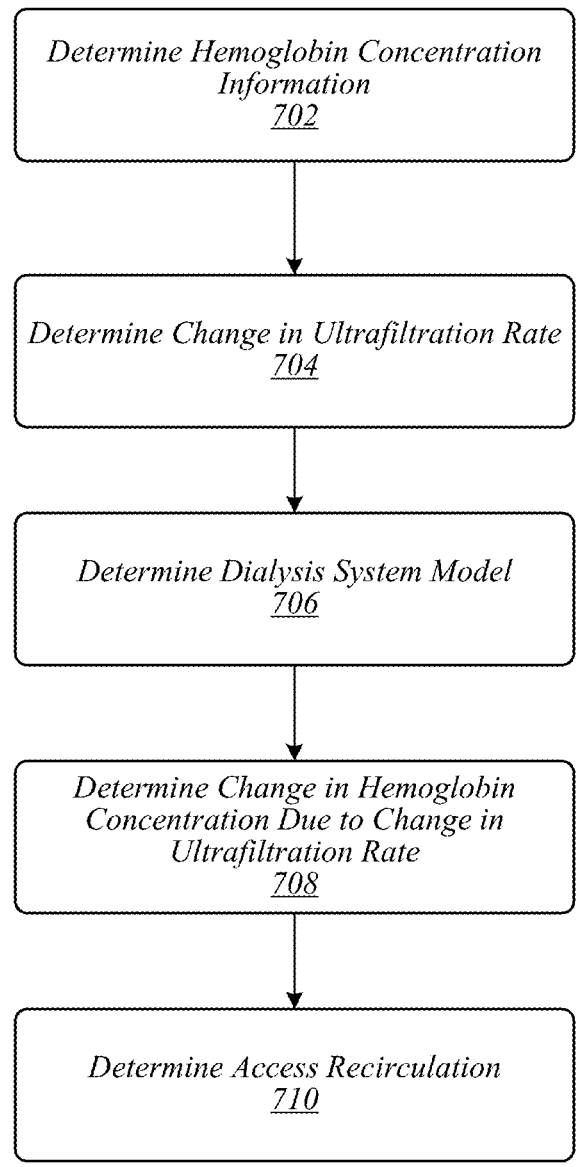
FIG. 7 illustrates an embodiment of a logic flow.

FIG. 7 illustrates an embodiment of a logic flow 700. Logic flow 700 may be representative of some or all of the operations executed by one or more embodiments described herein, such as apparatus 105, healthcare information exchange platform 205, and/or integrated care system 305 and/or 405. Although logic flow 700 is represented in FIG. 7 as occurring in a particular order, embodiments are not so limited, as blocks may be performed out of order, simultaneously, or not performed. In some embodiments, logic flow 700 may be representative of some or all of the operations of an AR measurement process.

At block 702, logic flow 700 may determine hemoglobin concentration information. For example, in some embodiments, a physiological measurement device 150a-n may include a hemoglobin concentration measurement device. In other embodiments, a physiological measurement device 150a-n may include a hematocrit measurement device, such as a CLM, operative to determine hematocrit measurement information. Hemoglobin concentration information may be determined from hematocrit measurement information. For example, hemoglobin concentration (for instance, in units of g/dL) may be equal to hematocrit (% packed cell volume (PCV))×about 0.3 (for instance, 0.34). In another example, hemoglobin concentration (for instance, in units of g/dL) may be equal to hematocrit (decimal fraction)×about 30 (for instance, 34). Other methods for determining hemoglobin concentration from hematocrit may also be used. Embodiments are not limited in this context.

At block 704, logic flow 700 may determine a change in the ultrafiltration rate of a dialysis system. For example, a first UFR (or $Q_{uf}$) at time $t_1$ may be determined and a second UFR at time $t_2$ may be determined. For instance, the first UFR may be about 10 mL/min and the second UFR may be about 50 mL/min, for a change in UFR of about 40 mL/min. In some embodiments, the first UFR may be a prescribed UFR.

Logic flow 700 may determine a dialysis system model at block 706. For example, a compartmental model (FIG. 5A) or a tubular model (FIG. 6A) may be used by logic flow 700.

At block 708, logic flow 700 may determine a change in hemoglobin concentration due to the change in UFR. For example, logic flow 700 may detect a change in UFR or may receive input indicating a change in UFR has or will occur. For a compartmental model, dialysis system 505 may be used to determine the change in hemoglobin concentration due to the change in UFR, represented, for instance, in the change in hemoglobin concentration depicted in graphs 905 and 1005. In another example, for a tubular model, dialysis system 605 may be used to determine the change in hemoglobin concentration due to the change in UFR, represented, for instance, in the change in hemoglobin concentration depicted in graphs 910 and 1010.

At block 710, logic flow 700 may determine AR. For example, in a compartmental model, mass balance processes 550, 552, 554, 556, and/or 558 may be used to determine AR based on the flow rate (for instance, $Q_b$ and/or $Q_{uf}$) and/or concentration information (for instance, $C_a$, $C_v$, $C_s$, $C_d$, $C_{vt}$, $C_{at}$, and/or the like). In another example, in a tubular model, mass balance processes 650, 652, 654, 656, and/or 658 may be used to determine AR based on the flow rate (for instance, $Q_b$ and/or $Q_{uf}$) and/or concentration information (for instance, $C_a$, $C_v$, $C_s$, $C_d$, $C_{vt}$, $C_{at}$, and/or the like). For example, a mass balance process may be solved for the value of AR based on known, assumed, estimated, predicted, and/or measured values (for instance, flow and/or concentration values). In another example, estimated, predicted, or otherwise determined values for AR may be used in mass balance processes to determine the correct AR value in which the mass balance process generates a value corresponding with measured, known, assumed, and/or estimated values. In various embodiments, AR may be determined according to the following:

$$AR\ [\%] = \frac{(Hgb_1 - Hgb_2)}{Qb\left(\dfrac{Hgb_1}{Q_b - Q_{uf,1}} - \dfrac{Hgb_2}{Q_b - Q_{uf,2}}\right)} \times 100,$$

Where, AR is access recirculation, $Q_{uf,1}$ is the (prescribed, initial, or first) ultrafiltration rate, $Q_{uf,2}$ is the perturbed (changed or second) ultrafiltration rate, $Q_b$ is the prescribed blood flow rate, $Hgb_1$ is the steady hemoglobin before perturbation of ultrafiltration rate, and $Hgb_2$ is the steady hemoglobin after the perturbation of ultrafiltration rate.

Experiment: Simulation of Compartmental Model and Tubular Model

Figure 8:
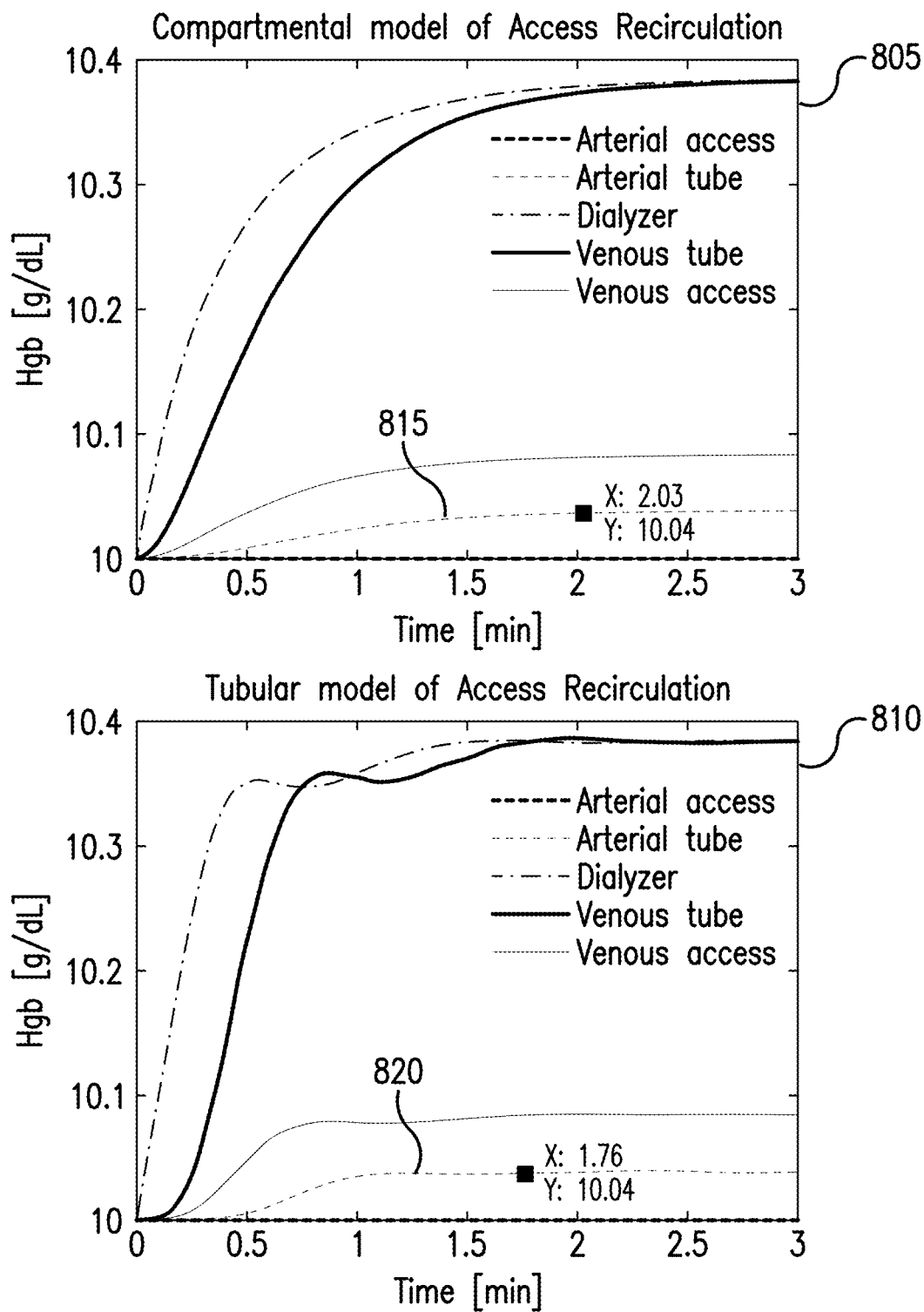
FIG. 8 illustrates graphs of model output for a compartmental model and a tubular model according to an embodiment.

A compartmental model and tubular model with appropriate initial and boundary conditions were simulated according to some embodiments. FIG. 8 depicts graphical output for a first simulation for a compartmental model of access recirculation (graph 805) and a tubular model of access recirculation (graph 810). When systemic Hgb concentration is 10 g/dL, the concentration measured by CLM was about 10.04 g/dL, if recirculation is 10%, $Q_b$ is about 300 mL/min, and UFR is about 10 mL/min. The compartmental model may take about 2 minutes to reach steady state, while a tubular model may take about 1.76 min to reach steady state. In FIG. 8, line 815 depicts concentration in the arterial compartment in graph 805 and line 820 depicts concentration at the end of the arterial tube in graph 810.

Figure 9:
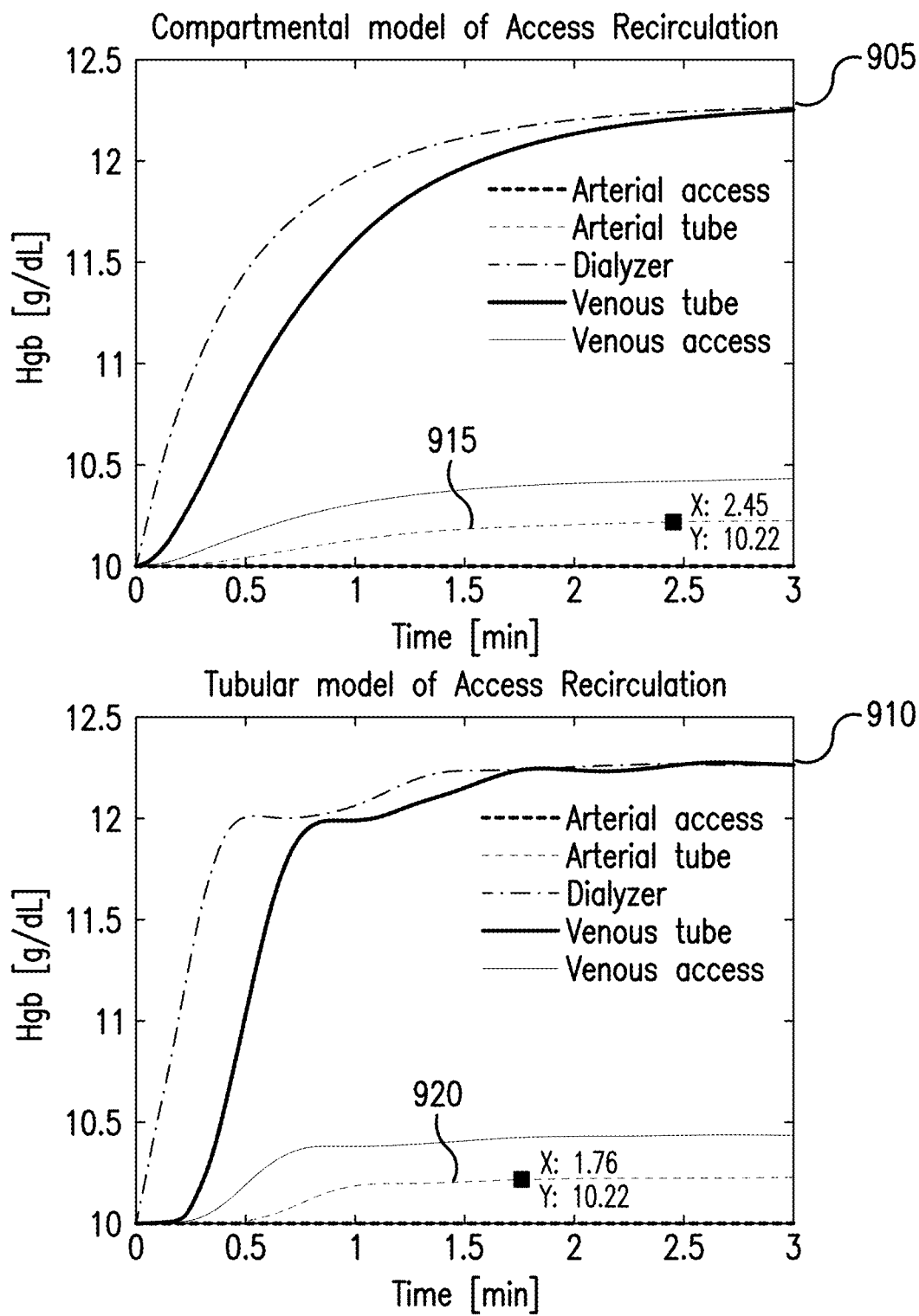
FIG. 9 illustrates graphs of model output for a compartmental model and a tubular model according to an embodiment.

In a second simulation, assuming AR is fixed at 10%, $Q_b$ is about 300 mL/min, and UFR is increased from about 10 mL/min to 50 mL/min, the simulated system may reach a new steady state to 10.22 g/dL in 2.45 min for the compartmental model and 1.75 min for the tubular model. The systemic Hgb concentration was kept fixed at 10 g/dL. FIG. 9 depicts graphical output for the second simulation for a compartmental model of access recirculation (graph 905) and a tubular model of access recirculation (graph 910). For the tubular model, the concentration at arterial tube is outlet plotted, since this is what is measured by CLM.

Figure 10:
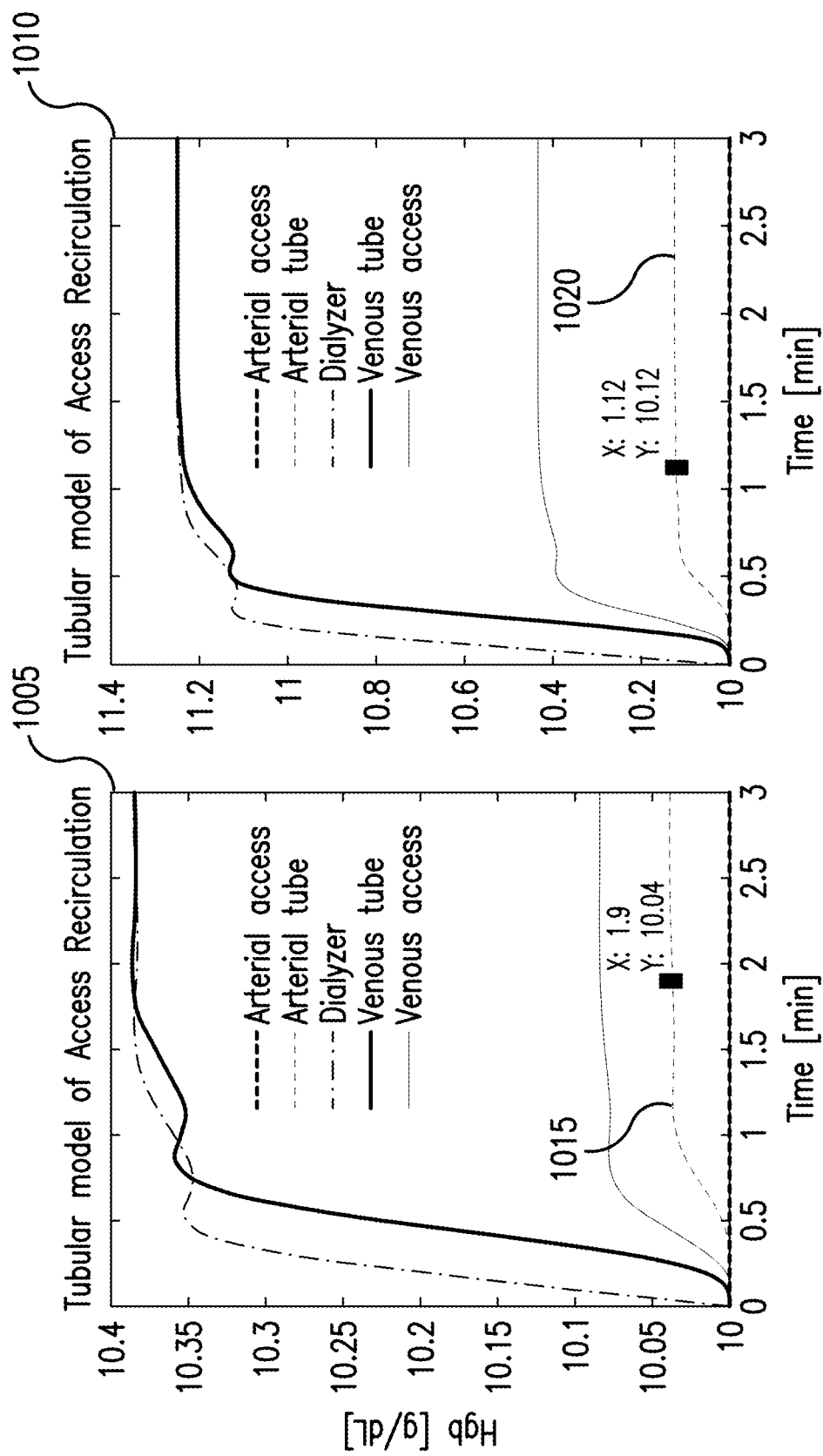
FIG. 10 illustrates graphs of model output for a tubular model according to an embodiment.
Figure 11:
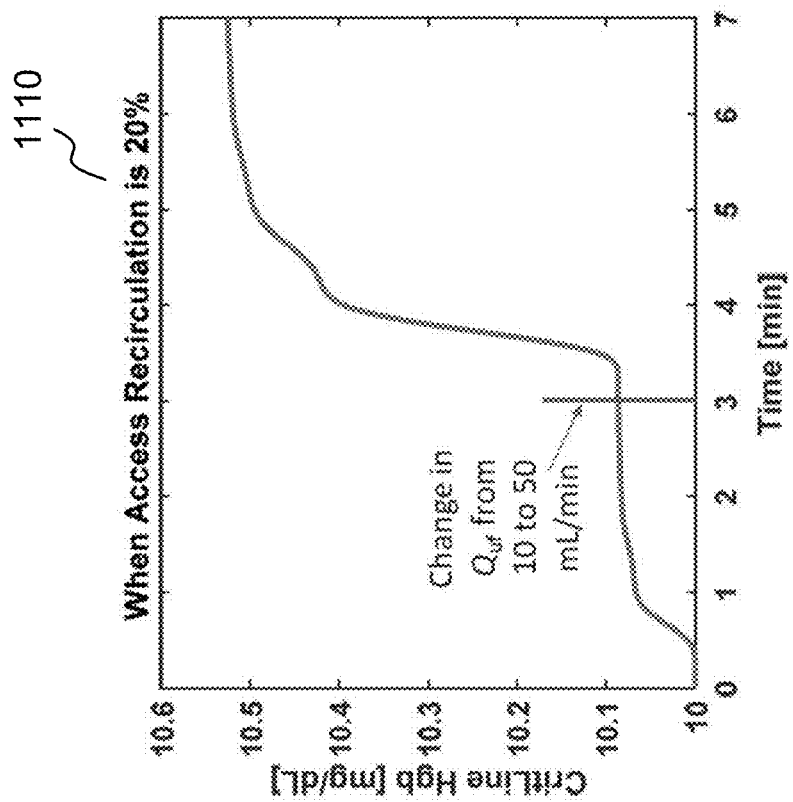
FIG. 11 illustrates graphs of model output for different access recirculation values for a tubular model according to an embodiment.
Figure 11:
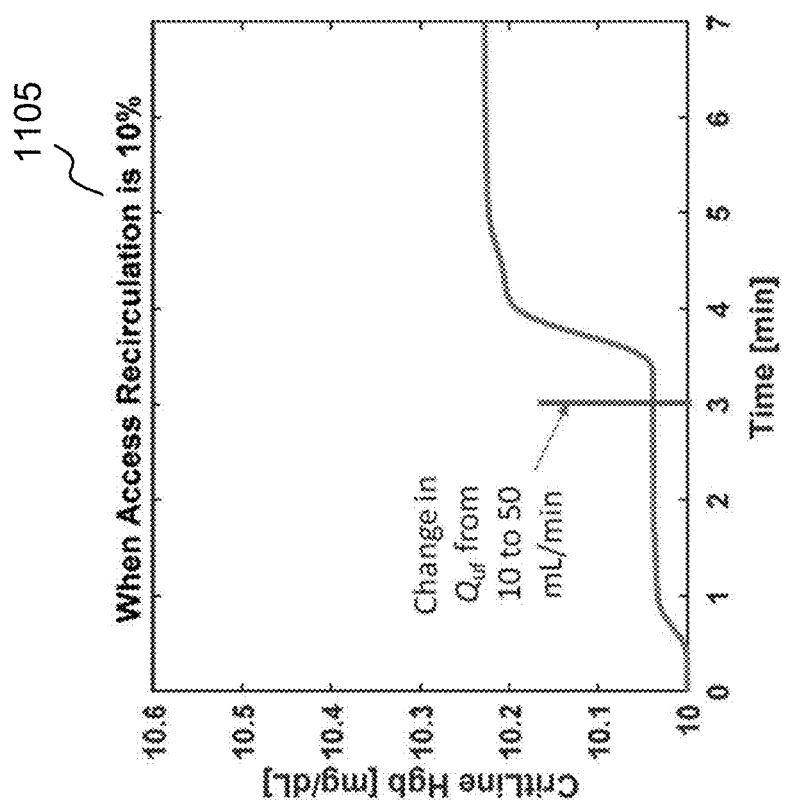

In a third simulation, to maximize signal strength, $Q_b$ and $Q_{uf}$ may be changed simultaneously, for example, in a tubular model. FIG. 10 depicts graphical output for the third simulation. In graph 1005, $Q_b$ is about 300 mL/min and $Q_{uf}$ is about 10 mL/min; in graph 1010 $Q_b$ is about 500 mL/min and $Q_{uf}$ is about 50 mL/min. Lines 1015 and 1020 denote the concentration at the end of the arterial tube, for example, as measured by CLM. FIG. 11 depicts a change in Hgb concentration for the tubular model measured by the CLM when the UFR is changed from a first UFR (for instance 10 mL/min) to a higher, second UFR (for instance, 50 mL/min) for different AR values. Graph 1105 depicts an AR of 10% and graph 1110 depicts an AR of 20%. For example, the UFR may be changed or perturbed from a known first UFR to a known second UFR. FIG. 11 depicts the corresponding change in Hgb concentration measured by the CLM, which is associated with the corresponding AR.

In some embodiments, an important assumption in the model simulations may be that systemic concentration does not change while the system achieves a new steady state, subjected to UFR perturbation. Ultrafiltration may causes increase in Hgb concentration in systemic blood also. Accordingly, some embodiments may assume that a change in systemic concentration may take more time to reflect at the arterial access compartment than the time taken by access recirculation and new measurement by CLM. For example, in a tubular model, the time taken to see the change in Hgb concentration may be about 1.75 min. In various embodiments, in the tubular model output, a decrease in concentration may occur for the dialyzer and venous tube. This decrease in concentration may be due to, inter alia, the time taken by AR stream to travel dialyzer fiber length followed by venous tube length. In a simulation in which the pump blood flow rate ($Q_b$) is increased, the fluctuation occurs faster and for a shorter period of time as depicted in graphs 1205 and 1210 of FIG. 12. In graph 1205, $Q_b$ is about 500 mL/min, and in graph 1210, $Q_b$ is about 800 mL/min; $Q_{uf}$ was constant at 10 mL/min for both graphs 1205 and 1210.

Figure 13:
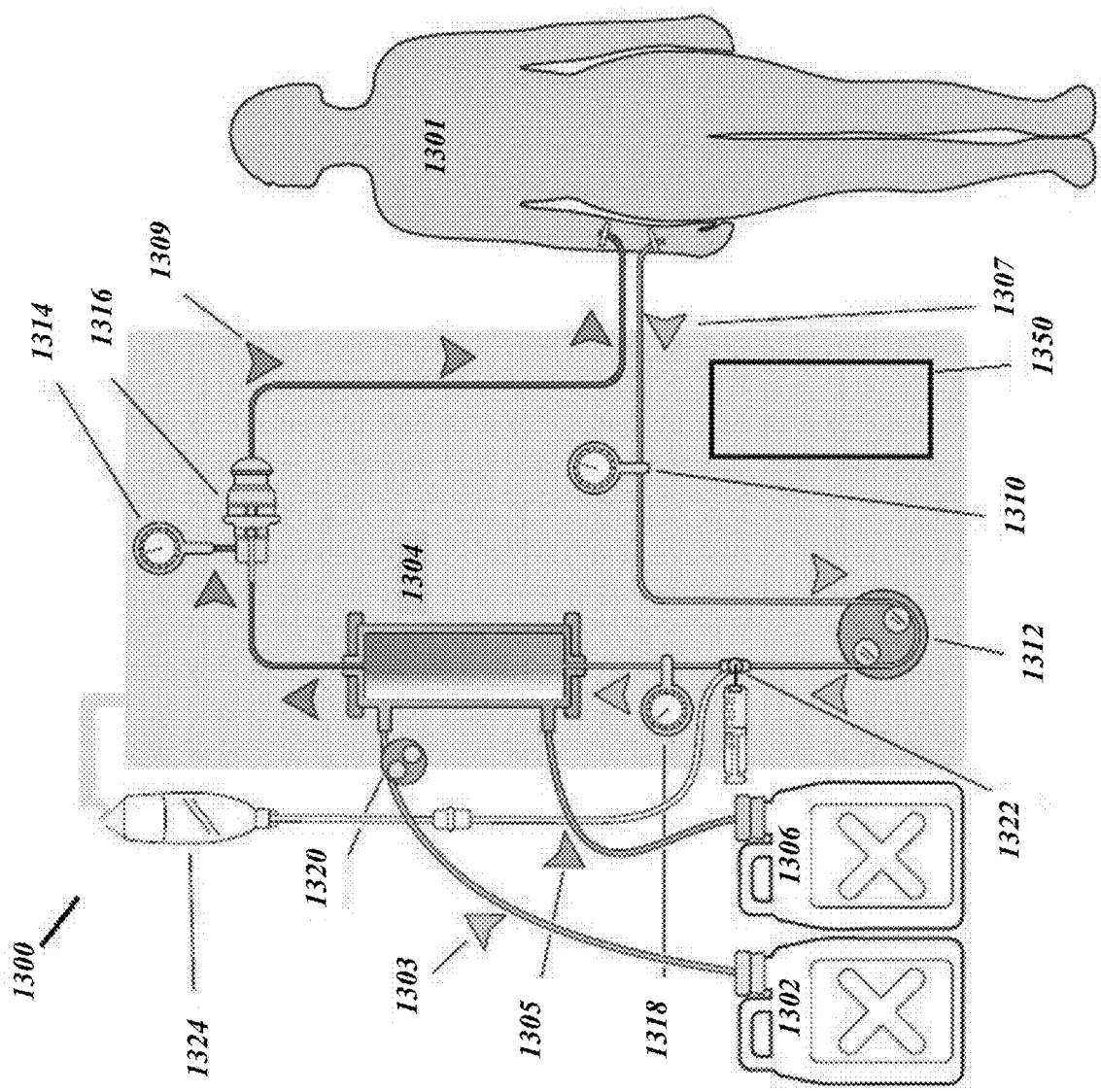
FIG. 13 illustrates an example hemodialysis system.

FIG. 13 illustrates a diagram of an exemplary embodiment of a dialysis system 1300 in accordance with the present disclosure. Dialysis system 1300 may be configured to provide hemodialysis (HD) treatment for a patient 1301. Fluid reservoir 1302 may deliver fresh dialysate to a dialyzer 1304 via tubing 1303, and reservoir 1306 may receive spent dialysate once it has passed through dialyzer 1304 via tubing 1305. A hemodialysis operation may filter particulates and/or contaminates from a patient's blood through a patient external filtration device, for example, a dialyzer 1304. As the dialysate is passed through dialyzer 1304, unfiltered patient blood is also passed into dialyzer 1304 via tubing 1307 and filtered blood is returned to patient 1301 via tubing 1309. Arterial pressure may be monitored via pressure sensor 1310, inflow pressure monitored via sensor 1318, and venous pressure monitored via pressure sensor 1314. An air trap and detector 1316 may ensure that air is not introduced into patient blood as it is filtered and returned to patient 1301. The flow of blood 1307 and the flow of dialysate may be controlled via respective pumps, including a blood pump 1312 and a fluid pump 1320. Heparin 1322, a blood thinner, may be used in conjunction with saline 1324 to ensure blood clots do not form or occlude blood flow through the system.

In some embodiments, dialysis system 1300 may include a controller 1350, which may be similar to computing device 110 and/or components thereof (for instance, processor circuitry 130). Controller 1350 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. In various embodiments, controller may receive and/or calculate hemoglobin concentrations, AR measurements, flow rates, and/or the like. Controller 1350 may also be operatively connected to and/or communicate with additional sensors or sensor systems, devices, and/or the like, although controller 1350 may use any of the data available on the patient's biologic functions or other patient parameters. For example, controller 1350 may send patient data to computing device 110, healthcare exchange platform 205, and/or integrated care system 305 and/or 405 to determine AR values according to some embodiments. Machine 1300 and/or components thereof, such as controller 1350, may be operably coupled to a hematocrit measurement device, CLM, hemoglobin concentration measurement device, and/or the like to facilitate processes performed by computing device 110, healthcare exchange platform 205, and/or integrated care system 305 and/or 405.

FIG. 14 illustrates an embodiment of an exemplary computing architecture 1400 suitable for implementing various embodiments as previously described. In various embodiments, the computing architecture 1400 may comprise or be implemented as part of an electronic device. In some embodiments, the computing architecture 1400 may be representative, for example, of computing device 110 and/or components of healthcare exchange platform 205 and/or integrated care system 305 and/or 405. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1400. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1400 includes various common computing elements, such as one or more processors, multi-core processors, co-processors, memory units, chip-sets, controllers, peripherals, interfaces, oscillators, timing devices, video cards, audio cards, multimedia input/output (I/O) components, power supplies, and so forth. The embodiments, however, are not limited to implementation by the computing architecture 1400.

As shown in FIG. 14, the computing architecture 1400 comprises a processing unit 1404, a system memory 1406 and a system bus 14014. The processing unit 1404 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1404.

The system bus 14014 provides an interface for system components including, but not limited to, the system memory 1406 to the processing unit 1404. The system bus 14014 can be any of several types of bus structure that may further interconnect to a memory bus (with or without a memory controller), a peripheral bus, and a local bus using any of a variety of commercially available bus architectures. Interface adapters may connect to the system bus 14014 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1406 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 14, the system memory 1406 can include non-volatile memory 1410 and/or volatile memory 1412. A basic input/output system (BIOS) can be stored in the non-volatile memory 1410.

The computer 1402 may include various types of computer-readable storage media in the form of one or more lower speed memory units, including an internal (or external) hard disk drive (HDD) 1414, a magnetic floppy disk drive (FDD) 1416 to read from or write to a removable magnetic disk 14114, and an optical disk drive 1420 to read from or write to a removable optical disk 1422 (e.g., a CD-ROM or DVD). The HDD 1414, FDD 1416 and optical disk drive 1420 can be connected to the system bus 14014 by a HDD interface 1424, an FDD interface 1426 and an optical drive interface 14214, respectively. The HDD interface 1424 for external drive implementations can include at least one or both of Universal Serial Bus (USB) and IEEE 14144 interface technologies.

The drives and associated computer-readable media provide volatile and/or nonvolatile storage of data, data structures, computer-executable instructions, and so forth. For example, a number of program modules can be stored in the drives and memory units 1410, 1412, including an operating system 1430, one or more application programs 1432, other program modules 1434, and program data 1436. In one embodiment, the one or more application programs 1432, other program modules 1434, and program data 1436 can include, for example, the various applications and/or components of apparatus 105, 205, 305, and/or 405.

A user can enter commands and information into the computer 1402 through one or more wire/wireless input devices, for example, a keyboard 14314 and a pointing device, such as a mouse 1440. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1404 through an input device interface 1442 that is coupled to the system bus 14014, but can be connected by other interfaces such as a parallel port, IEEE 1494 serial port, a game port, a USB port, an IR interface, and so forth.

A monitor 1444 or other type of display device is also connected to the system bus 14014 via an interface, such as a video adaptor 1446. The monitor 1444 may be internal or external to the computer 802. In addition to the monitor 1444, a computer typically includes other peripheral output devices, such as speakers, printers, and so forth.

The computer 1402 may operate in a networked environment using logical connections via wire and/or wireless communications to one or more remote computers, such as a remote computer 14414. The remote computer 14414 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1450 is illustrated. The logical connections depicted include wire/wireless connectivity to a local area network (LAN) 1452 and/or larger networks, for example, a wide area network (WAN) 1454. Such LAN and WAN networking environments are commonplace in offices and companies, and facilitate enterprise-wide computer networks, such as intranets, all of which may connect to a global communications network, for example, the Internet.

When used in a LAN networking environment, the computer 1402 is connected to the LAN 1452 through a wire and/or wireless communication network interface or adaptor 1456. The adaptor 1456 can facilitate wire and/or wireless communications to the LAN 1452, which may also include a wireless access point disposed thereon for communicating with the wireless functionality of the adaptor 1456.

When used in a WAN networking environment, the computer 1402 can include a modem 14514, or is connected to a communications server on the WAN 1454, or has other means for establishing communications over the WAN 1454, such as by way of the Internet. The modem 14514, which can be internal or external and a wire and/or wireless device, connects to the system bus 14014 via the input device interface 1442. In a networked environment, program modules depicted relative to the computer 1402, or portions thereof, can be stored in the remote memory/storage device 1450. It will be appreciated that the network connections shown are exemplary and other means of establishing a communications link between the computers can be used.

The computer 1402 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   at least one memory comprising instructions; and
   at least one processor coupled to the at least one memory to access the instructions, the instructions, when executed by the at least one processor, to cause the at least one processor to:
      during a dialysis treatment of a patient via a dialysis system:
         access a dialysis system model operative to quantify a change in a hemoglobin concentration of the patient due to a change in an ultrafiltration rate of the dialysis system, the dialysis system model based, at least in part, on a hemoglobin concentration in an arterial access compartment, a hemoglobin concentration in a venous access compartment, an ultrafiltration rate, and a dialyzer flow rate,
         determine a first hemoglobin concentration of the patient at a first ultrafiltration rate,
         determine a change in the first ultrafiltration rate to a second ultrafiltration rate, and
         determine a second hemoglobin concentration of the patient modified due to the second ultrafiltration rate based on the dialysis system model of the dialysis system, and determine an access recirculation value indicating a presence of an access recirculation condition for the patient based on the first hemoglobin concentration and the second hemoglobin concentration.

2. The apparatus of claim 1, further comprising a hematocrit measurement device comprising an inline monitor operative to measure hematocrit during dialysis treatment by the dialysis system.

3. The apparatus of claim 2, the first hemoglobin concentration or the second hemoglobin concentration determined based on hematocrit measurement information determined by the hematocrit measurement device.

4. The apparatus of claim 1, the dialysis system model comprising one of a compartmental model and a tubular model.

5. The apparatus of claim 1, the dialysis system model comprising an arterial access element, an arterial tube element, a hematocrit measurement device element, a dialyzer element, a venous tube element, and a venous access element.

6. The apparatus of claim 1, the dialysis system model comprising a tubular model comprising an arterial tube element, a dialyzer element, and a venous tube element configured as a tubular flow system.

7. The apparatus of claim 1, the instructions, when executed by the at least one processor, to cause the at least one processor to determine the access recirculation value based on at least one mass balance process of the dialysis system model.

8. The apparatus of claim 7, the dialysis system model comprising a compartmental model,
wherein the instructions, when executed by the at least one processor, to cause the at least one processor to determine the access recirculation value using at least one of the following hemoglobin mass balance processes:

$$\frac{d(C_a V_a)}{dt} = Q_s C_s - (1 - AR)Q_b C_a - (Q_s - (1 - AR)Q_b)C_a,$$

$$\frac{d(C_{at} V_{at})}{dt} = (1 - AR)Q_b C_a + AR \cdot Q_b C_{vt} - Q_b C_{at},$$

$$\frac{d(C_d V_d)}{dt} = Q_b C_{at} - (Q_b - Q_{uf})C_d,$$

$$\frac{d(C_{vt} V_{vt})}{dt} = (Q_b - Q_{uf})C_d - AR \cdot Q_b C_{vt} - (Q_b - Q_{uf} - AR \cdot Q_b)C_{vt},$$

$$\frac{d(C_v V_v)}{dt} = (Q_s - (1 - AR)Q_b)C_a + (Q_b - Q_{uf} - AR \cdot Q_b)C_{vt} - (Q_s - Q_{uf})C_v,$$

where $C_a$ is a hemoglobin concentration in an arterial access compartment, $V_a$ is a volume of the arterial access compartment, $C_{at}$ is a hemoglobin concentration in an arterial tube compartment, $V_{at}$ is a volume of the arterial tube compartment, $C_d$ is a hemoglobin concentration in a dialysis compartment, $V_d$ is a volume of the dialysis compartment, $C_{vt}$ is a hemoglobin concentration in a venous tube compartment, $V_{vt}$ is a volume of the venous tube compartment, $C_v$ is a hemoglobin concentration in a venous access compartment, $V_v$ is a volume of the venous access compartment, Qs is a systemic flow rate, $Q_b$ is a dialyzer flow rate, $Q_a$ is an arterial access flow rate, $Q_{uf}$ is an ultrafiltration rate, $C_s$ is a systemic hemoglobin concentration, and AR is the access recirculation value.

9. The apparatus of claim 7, the dialysis system model comprising a tubular model,
wherein the instructions, when executed by the at least one processor, to cause the at least one processor to determine the access recirculation value using at least one of the following hemoglobin mass balance processes:

$$\frac{d(C_a V_a)}{dt} = Q_s C_s - (1 - AR)Q_b C_a - (Q_s - (1 - AR)Q_b)C_a,$$

$$\frac{\partial C_{at}}{\partial t} = -\frac{Q_b}{A_{tube}} \frac{\partial C_{at}}{\partial x},$$

$$\frac{\partial C_d}{\partial t} = -\frac{1}{NA} \frac{\partial}{\partial x}(QC_d),$$

$$\frac{\partial C_{vt}}{\partial t} = -\frac{Q_b - Q_{uf}}{A_{tube}} \frac{\partial C_{vt}}{\partial x},$$

$$\frac{d(C_v V_v)}{dt} =$$
$$(Q_s - (1 - AR)Q_b)C_a + (Q_b - Q_{uf} - AR \cdot Q_b)C_{vt} - (Q_s - Q_{uf})C_v.$$

where $V_v$ is a volume of the venous access compartment, $V_a$ is a volume of the arterial access compartment, $C_a$ is a hemoglobin concentration in an arterial access compartment, $C_{at}$ is a hemoglobin concentration in an arterial tube compartment, $C_d$ is a hemoglobin concentration in a dialysis compartment, $C_{vt}$ is a hemoglobin concentration in a venous tube compartment, $C_v$ is a hemoglobin concentration in a venous access compartment, Qs is a systemic flow rate, $C_s$ is a systemic hemoglobin concentration, $Q_b$ is a dialyzer flow rate, $Q_a$ is an arterial access flow rate, $Q_{uf}$ is an ultrafiltration rate, $A_{tube}$ is an area of a tube, and AR is the access recirculation value, and x is a variable.

10. A method, comprising:
during a dialysis treatment of a patient via a dialysis system:
access a dialysis system model operative to quantify a change in a hemoglobin concentration of the patient due to a change in an ultrafiltration rate of the dialysis system, the dialysis system model based, at least in part, on a hemoglobin concentration in an arterial access compartment, a hemoglobin concentration in a venous access compartment, an ultrafiltration rate, and a dialyzer flow rate;
determine a first hemoglobin concentration of the patient at a first ultrafiltration rate;
determine a change in the first ultrafiltration rate to a second ultrafiltration rate;
determine a second hemoglobin concentration of the patient modified due to the second ultrafiltration rate based on the dialysis system model of the dialysis system; and
determine an access recirculation value indicating a presence of an access recirculation condition for the patient based on the first hemoglobin concentration and the second hemoglobin concentration.

11. The method of claim 10, further comprising measuring via a hematocrit measurement device comprising an inline monitor operative to measure hematocrit during dialysis treatment by the dialysis system.

12. The method of claim 11, the first hemoglobin concentration or the second hemoglobin concentration determined based on hematocrit measurement information determined by the hematocrit measurement device.

13. The method of claim 10, the dialysis system model comprising one of a compartmental model and a tubular model.

14. The method of claim 10, the dialysis system model comprising an arterial access element, an arterial tube element, a hematocrit measurement device element, a dialyzer element, a venous tube element, and a venous access element.

15. The method of claim 10, the dialysis system model comprising a tubular model comprising an arterial tube element, a dialyzer element, and a venous tube element configured as a tubular flow system.

16. The method of claim 10, comprising determining the access recirculation value based on at least one mass balance process of the dialysis system model.

17. The method of claim 10, the dialysis system model comprising a compartmental model, further comprising determining the access recirculation value using at least one of the following hemoglobin mass balance processes:

$$\frac{d(C_a V_a)}{dt} = Q_s C_s - (1 - AR)Q_b C_a - (Q_s - (1 - AR)Q_b)C_a,$$

$$\frac{d(C_{at} V_{at})}{dt} = (1 - AR)Q_b C_a + AR \cdot Q_b C_{vt} - Q_b C_{at},$$

$$\frac{d(C_d V_d)}{dt} = Q_b C_{at} - (Q_b - Q_{uf})C_d,$$

$$\frac{d(C_{vt} V_{vt})}{dt} = (Q_b - Q_{uf})C_d - AR \cdot Q_b C_{vt} - (Q_b - Q_{uf} - AR \cdot Q_b)C_{vt},$$

$$\frac{d(C_v V_v)}{dt} = (Q_s - (1 - AR)Q_b)C_a + (Q_b - Q_{uf} - AR \cdot Q_b)C_{vt} - (Q_s - Q_{uf})C_v.$$

where $C_a$ is a hemoglobin concentration in an arterial access compartment, $V_a$ is a volume of the arterial access compartment, $C_{at}$ is a hemoglobin concentration in an arterial tube compartment, $V_{at}$ is a volume of the arterial tube compartment, $C_d$ is a hemoglobin concentration in a dialysis compartment, $V_d$ is a volume of the dialysis compartment, $C_{vt}$ is a hemoglobin concentration in a venous tube compartment, $V_{vt}$ is a volume of the venous tube compartment, $C_v$ is a hemoglobin concentration in a venous access compartment, $V_v$ is a volume of the venous access compartment, Qs is a systemic flow rate, $Q_b$ is a dialyzer flow rate, $Q_a$ is an arterial access flow rate, $Q_{uf}$ is an ultrafiltration rate, $C_s$ is a systemic hemoglobin concentration, and AR is the access recirculation value.

18. The method of claim 16, the dialysis system model comprising a tubular model, further comprising determining the access recirculation value using at least one of the following hemoglobin mass balance processes:

$$\frac{d(C_a V_a)}{dt} = Q_s C_s - (1 - AR)Q_b C_a - (Q_s - (1 - AR)Q_b)C_a,$$

$$\frac{\partial C_{at}}{\partial t} = -\frac{Q_b}{A_{tube}} \frac{\partial C_{at}}{\partial x},$$

$$\frac{\partial C_d}{\partial t} = -\frac{1}{NA} \frac{\partial}{\partial x}(QC_d),$$

$$\frac{\partial C_{vt}}{\partial t} = -\frac{Q_b - Q_{uf}}{A_{tube}} \frac{\partial C_{vt}}{\partial x},$$

$$\frac{d(C_v V_v)}{dt} = (Q_s - (1 - AR)Q_b)C_a + (Q_b - Q_{uf} - AR \cdot Q_b)C_{vt} - (Q_s - Q_{uf})C_v.$$

where $V_v$ is a volume of the venous access compartment, $V_a$ is a volume of the arterial access compartment, $C_a$ is a hemoglobin concentration in an arterial access compartment, $C_{at}$ is a hemoglobin concentration in an arterial tube compartment, $C_d$ is a hemoglobin concentration in a dialysis compartment, $C_{vt}$ is a hemoglobin concentration in a venous tube compartment, $C_v$ is a hemoglobin concentration in a venous access compartment, Qs is a systemic flow rate, $C_s$ is a systemic hemoglobin concentration, $Q_b$ is a dialyzer flow rate, $Q_a$ is an arterial access flow rate, $Q_{uf}$ is an ultrafiltration rate, $A_{tube}$ is an area of a tube, and AR is the access recirculation value, and x is a variable.

19. The method of claim 10, comprising:
determining a dialysis complication event responsive to the access recirculation value being over a threshold value, and
providing, via a computing device associated with the dialysis system, a dialysis complication response comprising at least one of displaying a dialysis complication warning, displaying a stenosis warning, stopping the dialysis treatment.

20. The method of claim 19, comprising administering treatment to the patient based on the access recirculation value via at least one of: determining operating parameters for the dialysis system using the access recirculation value or monitoring for a dialysis complication based on the access recirculation value.

* * * * *